United States Patent
Guirao et al.

(10) Patent No.: US 6,511,180 B2
(45) Date of Patent: Jan. 28, 2003

(54) DETERMINATION OF OCULAR REFRACTION FROM WAVEFRONT ABERRATION DATA AND DESIGN OF OPTIMUM CUSTOMIZED CORRECTION

(75) Inventors: Antonio Guirao, Murcia (ES); David R. Williams, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/969,600

(22) Filed: Oct. 4, 2001

(65) Prior Publication Data

US 2002/0140902 A1 Oct. 3, 2002

Related U.S. Application Data

(60) Provisional application No. 60/238,465, filed on Oct. 10, 2000.

(51) Int. Cl.[7] .................................................. A61B 3/10
(52) U.S. Cl. ...................................... 351/211; 351/221
(58) Field of Search ................................ 351/205, 211, 351/212, 219, 246, 247, 221; 606/4, 5; 356/121, 122, 123

(56) References Cited

U.S. PATENT DOCUMENTS

| | | | |
|---|---|---|---|
| 5,777,719 A | 7/1998 | Williams et al. ............ 351/212 |
| 5,949,521 A | * 9/1999 | Williams et al. ............ 351/246 |
| 6,050,687 A | 4/2000 | Bille et al. ................... 351/212 |
| 6,086,204 A | 7/2000 | Magnante .................... 351/212 |
| 6,199,986 B1 | 3/2001 | Williams et al. ............ 351/221 |
| 6,299,311 B1 | * 10/2001 | Williams et al. ............ 351/221 |

FOREIGN PATENT DOCUMENTS

WO    WO 99/27334 A1    6/1999

* cited by examiner

Primary Examiner—George Manuel
(74) Attorney, Agent, or Firm—Blank Rome Comisky & McCauley LLP

(57) ABSTRACT

Ocular refraction is determined from wavefront aberration data, and an optimum customized correction is designed. The eye's wave aberration is measured by using a detector such as a Shack-Hartmann detector. From the aberration, an image metric is calculated, and the second-order aberrations which optimize that metric are determined. From that optimization, the refractive correction required for the eye is determined. The image metric is one of several metrics indicating the quality of the image on the retinal plane or a proxy for such a metric. The required refractive correction can be used to form a lens or to control eye surgery. If it is possible to detect more aberrations than can be corrected, those aberrations are corrected which most affect vision, or for which the eye's error tolerance is lowest.

76 Claims, 19 Drawing Sheets

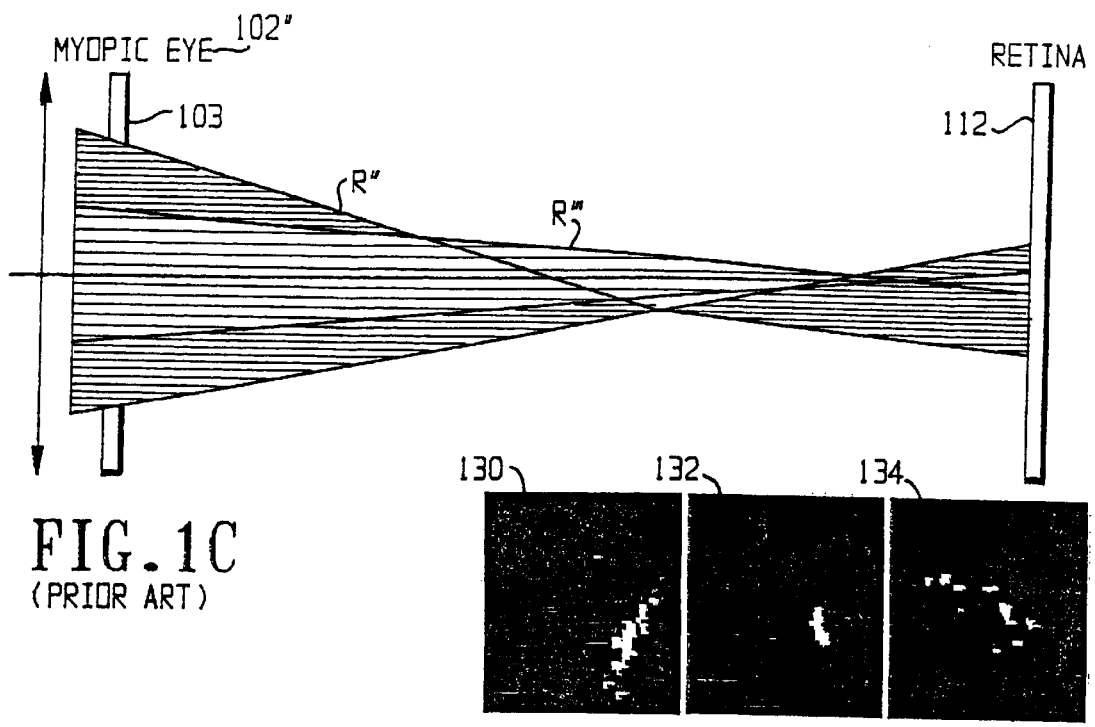
FIG.1C
(PRIOR ART)
FIG.1D REFRACTION FROM METHODS (1) AND (2) FAIL WHEN
(PRIOR ART) HIGHER-ORDER ABERRATIONS INCREASE
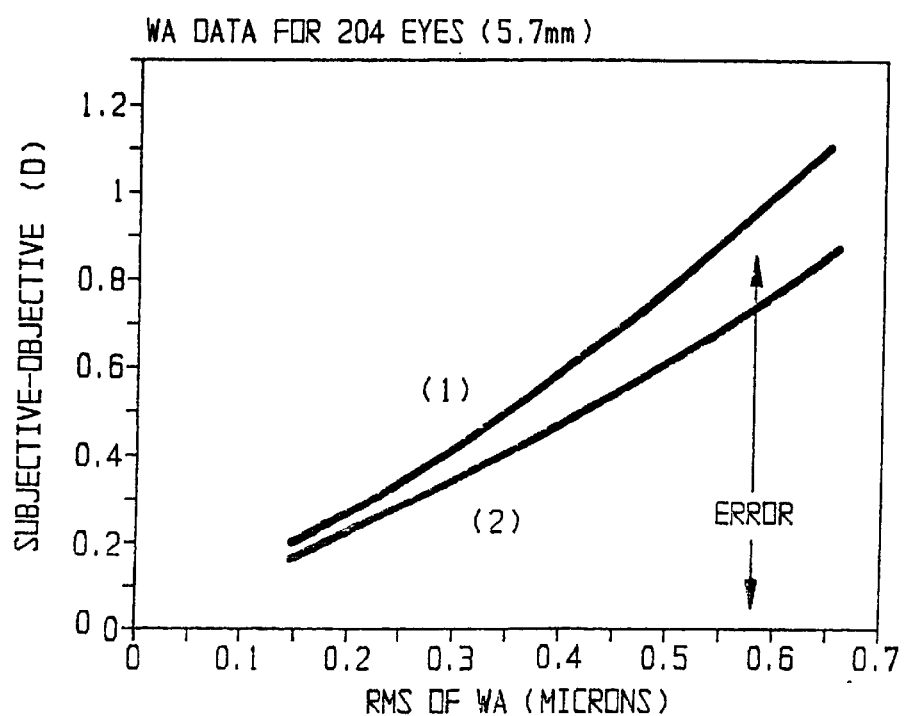

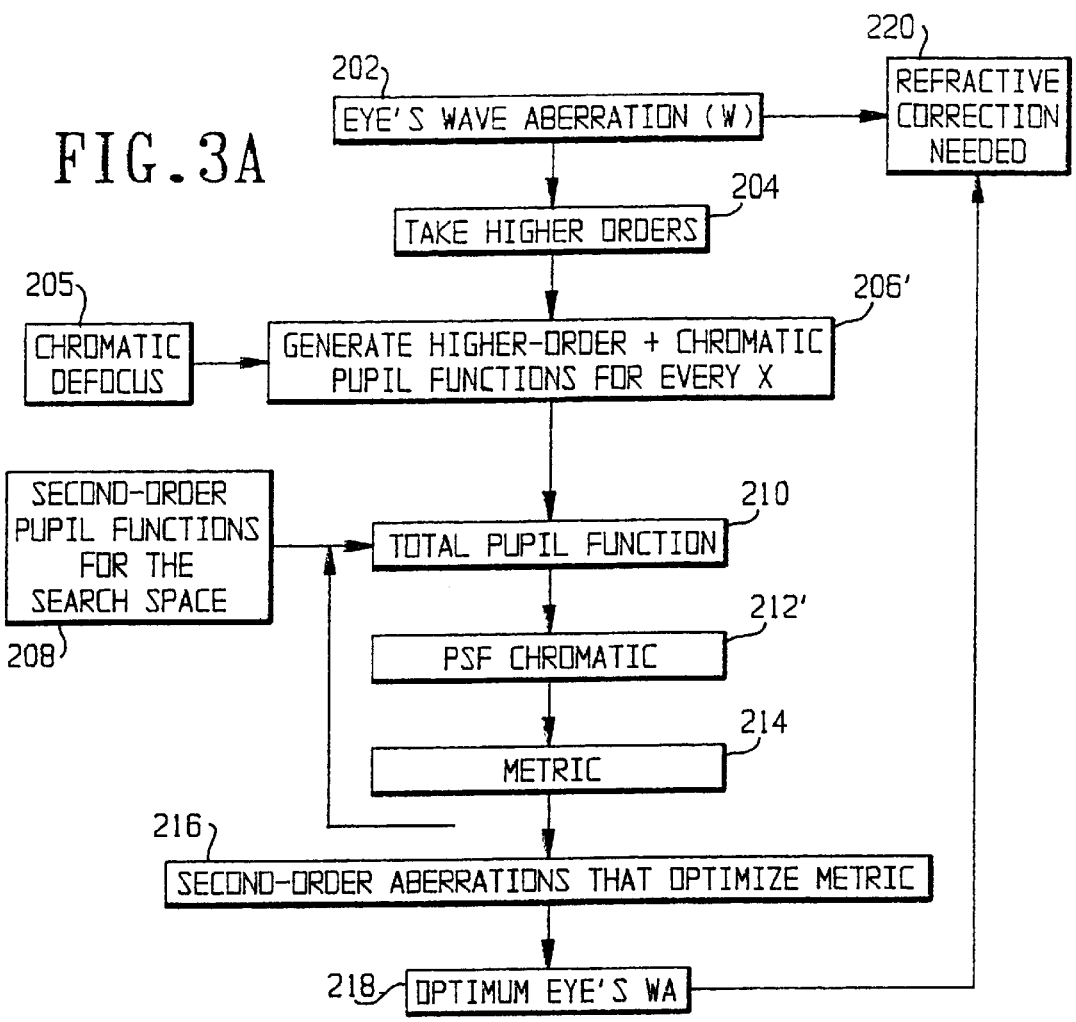
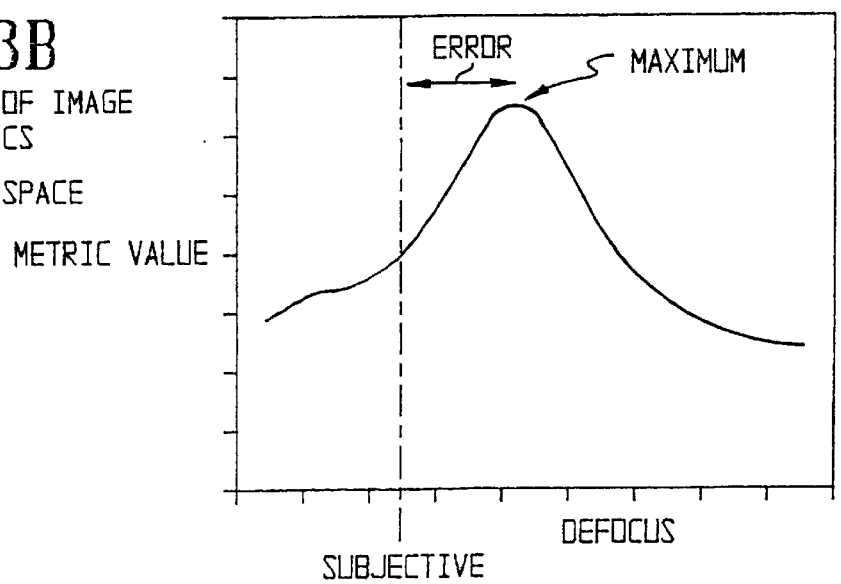

| WEYE | CORRECTING LENS | WOPTIMUM |
|---|---|---|
| -4.553 | | 0.350 |
| -0.833 | ? | -0.550 |
| -0.312 | ? | 0.250 |
| 0.095 | ? | 0.095 |
| 0.165 | | 0.165 |
| -0.083 | | -0.083 |
| -0.335 | | -0.335 |
| -0.016 | | -0.016 |
| -- -- | | -- -- |

SPHERE = 3.75 D
CYLINDER = -0.75 D x 120

RMSE BETWEEN SUBJECTIVE AND OBJECTIVE REFRACTION (ACROSS 6 EYES)

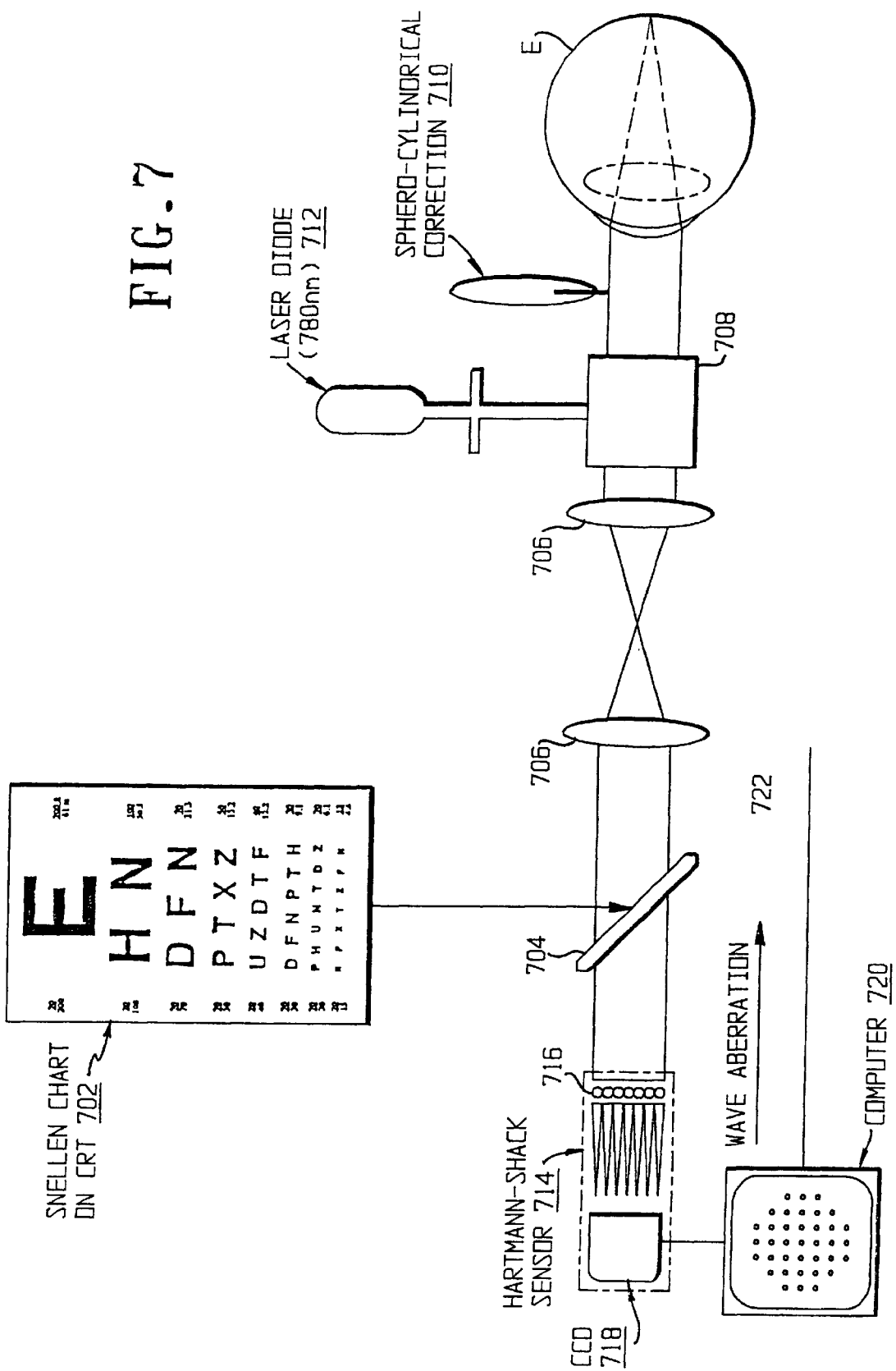

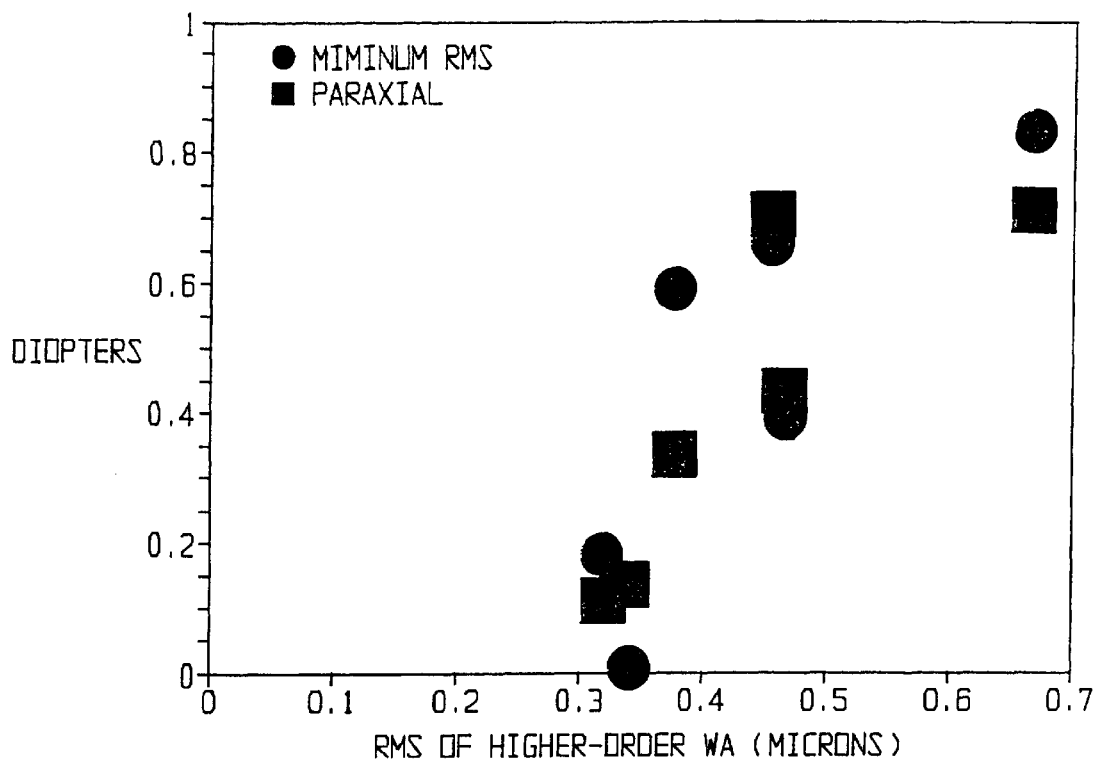
FIG. 10  HIGHER-ORDER AFFECTS REFRACTION
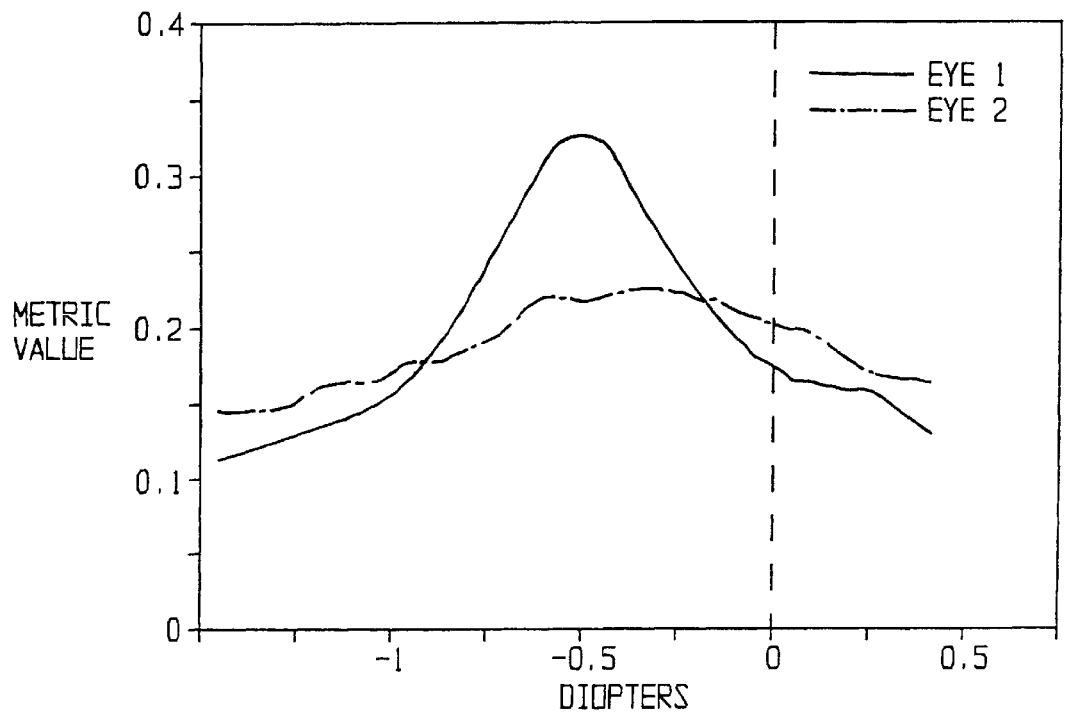
FIG. 11  HIGHER-ORDER AERRATIONS ALSO INFLLUENCE THE TOLERANCE TO REFRACTIVE ERRORS

DETERMINATION OF OCULAR REFRACTION FROM WAVEFRONT ABERRATION DATA AND DESIGN OF OPTIMUM CUSTOMIZED CORRECTION

REFERENCE TO RELATED APPLICATION

This application claims the benefit of U.S. Provisional Application No. 60/238,465, filed Oct. 10, 2000, whose disclosure is hereby incorporated by reference in its entirety into the present disclosure.

DESCRIPTION OF RELATED ART

Various objective techniques (retinoscopy, autorefraction, photorefraction) can be used to measure the spherical and cylindrical refractive errors of the human eye. They are fast and constitute an attractive alternative to performing a subjective refraction. Objective refraction is not only useful but often essential, for example, when examining young children and patients with mental or language difficulties. However, one major concern is the ability to properly determine objectively the refraction of the observer. Since all those objective methods are based on the light reflected from the retina and emerging from the eye, the ocular aberrations reduce the accuracy of the measurement. The eye suffers from many higher-order aberrations beyond defocus and astigmatism, which introduce defects on the pattern of light detected. Thus, photorefractive methods are based on paraxial optical analysis, and it has been shown that there can be a significant degree of measurement uncertainty when the spherical aberration of the normal human eye is considered. Aberrations also influence the retinoscopic measure. Although autorefractors provide reliable measurements of the refractive state of the eye, their limitations in accuracy and repeatability are well known. For example, there are discrepancies between autorefractive and subjective measurements, especially with astigmatism, or when the degree of ametropia is large. Such discrepancies are described in M. Elliott et al, "Repeatability and accuracy of automated refraction: A comparison of the Nikon NRK-8000, the Nidek AR-1000, and subjective refraction," Optom. Vis. Sci. 74,434–438, 1997; J. J. Walline et al, "Repeatability and validity of astigmatism measurements," J. Refract. Surgery 15, 23–31, 1999; and A. M. Thompson et al "Accuracy and precision of the Tomey ViVA infrared photorefractor," Optom. Vis. Sci. 73, 644–652, 1996. Also, retinoscopy and autorefraction usually disagree to some extent, as described in E. M. Harvey et al, "Measurement of refractive error in Native American preschoolers: Validity and reproducibility of autorefraction," Optom. Vis Sci. 77, 140–149, 2000.

Patients' preference with regard to autorefraction is described in M. A. Bullimore et al, "Patient Acceptance of Auto-Refractor and Clinician Prescriptions: A Randomized Clinical Trial," Visual Science and its Applications, 1996 Technical Digest Series, Vol. 1, Optical Society of America, Washington, D.C., pp. 194–197, and in M. A. Bullimore et al, "The Repeatability of Automated and Clinician Refraction," Optometry and Vision Science, Vol 75, No. 8, August, 1998, pp. 617–622. Those articles show that patients prefer the clinician's refraction; for example, the former article states that the autorefractor has a rejection rate around 11% higher than the clinician. The difference in rejection rates suggests that autorefraction is less accurate than the clinician's prescription. Thus, the state of the art in autorefraction provides room for improvement.

In that context, the development of an objective method that makes use of the higher-order aberrations of the eye and provides accurate estimates of the subjective refraction is an important challenge. Such a method would be extremely useful, for example, to refine refractive surgery. As more patients inquire about refractive surgical procedures, the accurate measurement of refractive errors prior to surgery becomes more important in assessing refractive outcome. Another important issue regards the aging of the eye. A difference has been found between subjective refraction and autorefraction for different age groups. That difference probably comes from the fact that the ocular aberrations increase with age. The age dependency is described in L. Joubert et al, "Excess of autorefraction over subjective refraction: Dependence on age," Optom. Vis. Sci. 74,439–444, 1997, and in A. Guirao et al, "Average optical performance of the human eye as a function of age in a normal population," Ophth. Vis. Sci. 40, 203–213, 1999. An objective method that considers the particular aberration pattern of the subject would provide reliable estimates for all the age groups. Such a method could also automatically give a value of refraction customized for every pupil size and light level, since both aberrations increase with pupil size and visual acuity depends on luminance conditions.

The higher-order aberrations of the eye can be now measured quickly, accurately and repetitively, for instance, with a Shack-Hartmann sensor. A method and apparatus for doing so are taught in U.S. Pat. No. 5,777,719 to Williams et al. It seems then almost mandatory to optimize the use of this new information in a more accurate instrument.

The simplest case of vision correction is shown in FIG. 1A, in which the only error is of focus. That is, the rays R passing through the edge of the pupil 103 of the eye 102 are focused on a paraxial plane 110 which is spatially separated from the plane 112 of the retina. Accordingly, the only correction required is to shift the plane of focus from the paraxial plane 110 to the retinal plane 112. The images before, at and after the paraxial plane 110 are shown as 124, 126 and 128, respectively.

The diagram in FIG. 1B shows an example of the image formation by a myopic eye 102' with negative spherical aberration. Without spherical aberration, all the rays R' would focus on the paraxial plane 110, and then the refraction of the eye would be calculated from the spherical negative lens required to displace the focus plane to the plane 112 lying on the retina. However, due to spherical aberration, the rays R passing through the edge of the pupil 103 converge at a plane 104 closer to the eye (marginal plane). That simple example shows how the distribution of rays in different planes produces images 114–122 with different quality. The refraction of that eye should be the one required for displacing a plane of "best image" to the retina.

A similar phenomenon occurs when astigmatism must be corrected. Depending on the higher-order aberrations of the eye, to maximize the image quality, the amount of astigmatism to correct could be different, beyond the paraxial zone, from that corresponding to the Sturm's interval (distance between the two focal planes determined by astigmatism).

Such a situation is shown in FIG. 1C. The rays R" and R'" from different locations in the pupil 103 of the eye 102" have focal points which are not coincident or even coaxial. Thus, the images taken at various locations are shown as 130, 132 and 134. In cases in which not all aberrations can be corrected, or in which all aberrations can be only partially corrected, it is necessary to determine which of the images 130, 132 and 134 is the best image.

The best image is not, or at least not necessarily, achieved by correcting the defocus and astigmatism corresponding to the paraxial approximation, which does not consider the effect of higher order aberrations. The question then is what is such a "best image." By a geometrical ray tracing the answer is that the best image would correspond to a plane where the size of the spot is minimum. That plane, shown in FIG. 1B as 106, is called the plane of least confusion (LC) and, for example, for a system aberrated with spherical aberration lies at ¾ of the distance between the paraxial and marginal planes. Another candidate is the plane 108 where the root-mean-square (RMS) radius of the spot is minimum. In the example of FIG. 1B, that plane lies midway between the marginal and paraxial planes. However, the spots determined geometrically do not accurately reflect the point spread function (PSF), which is the computed retinal image based on the results of the wavefront sensor and which should be calculated based on the diffraction of the light at the exit pupil. The distribution of light in a real image is usually very different from the image predicted geometrically with ray tracing. Any consideration about image quality should be done using diffraction theory.

The higher-order aberrations are combined with lower-order aberrations, which is known as "balancing." One of the main properties of the popular Zernike polynomials is that they represent balanced aberrations. Second-order polynomials, $Z_2^{0,\pm 2}$, represent defocus and astigmatism. For instance, spherical aberration is balanced with defocus in the term $Z_0^4$; the terms $Z_4^{\pm 2}$ are balanced with astigmatism, etc. The aberration balancing is an attractive concept in the sense that a minimum RMS of the aberrated wavefront suggests the achievement of the best image. Hence, the RMS of the wave aberration has been used as a measure of how aberrated an eye is and as a metric of image quality: the lower the RMS, the better the image quality. A fact that has supported that use is that the RMS correlates, for small aberrations, with another popular metric also used as a criterion of image quality, the Strehl ratio, defined as the peak of irradiance of the PSF. A large value of Strehl ratio indicates a good image quality. For small aberrations, Strehl ratio and RMS of the wave aberration are inversely proportional: when the Strehl ratio is maximum, the RMS is minimum. Several equations have been derived to express that relationship; one of the best known is:

$$S = \exp\left(-\left(\frac{2\pi}{\lambda} RMS\right)^2\right), \quad (1)$$

where S is the Strehl ratio and $\lambda$ is the wavelength.

The wave aberration is usually decomposed into Zernike basis functions after being measured, $W = \Sigma a_n^m Z_n^m$. An advantage of that is that the RMS of the wave aberration can then be obtained easily from the Zernike coefficients: $RMS^2 = \Sigma(a_n^m)^2$. Thus, any correction of the refractive errors of the eye, or of a set of higher-order aberrations, could be determined by setting to zero the corresponding Zernike coefficients ($a_2^{0,\pm 2}=0$ to correct refractive errors, or for example $a_3^{\pm 1}=0$ to correct coma). But, again, the image analysis based on diffraction shows the failure in general of that idea. When aberrations are large, a maximum Strehl ratio can be obtained with nonoptimally balanced aberrations (i.e., not a minimum in the RMS). More concretely, when the RMS of the wave aberration is larger than about 0.15 wavelengths, Eq. (1) is not longer valid. In comparison, the value for example of the spherical aberration of the normal average eye is 3–4 wavelengths for a pupil diameter of 6 mm. Therefore, the sphere and cylinder required to prescribe refraction and achieve the best image quality can not be obtained from the assumption of minimum RMS. The same occurs if one pretends to correct spherical aberration or coma, for instance. The balanced secondary spherical aberration (polynomial $Z_6^0$) and the balanced secondary coma ($Z_5^{\pm 1}$) do not give the maximum Strehl ratio for large aberrations.

The RMS minimization technique uses the coefficients $a_0^2$ and $a_2^{\pm 2}$ from the Zernike expansion and results in the correction of defocus and astigmatism. The paraxial technique extracts the total defocus and astigmatism in the wave aberration.

Both of the above techniques, which are based on the pupil plane and use the data of the wave aberration itself, fail when higher-order aberrations increase. In particular, the difference between the subjective and objective determinations of the aberration increases with the RMS of the wavefront aberration, as shown in FIG. 1D, in which curve (1) indicates the RMS minimization technique and curve (2) indicates the paraxial technique. The higher-order aberration in the population has been found to average $0.3\mu$, as shown in FIG. 1E. As a consequence, the above-noted techniques do not work for approximately half of the population and can introduce errors of up to one diopter.

SUMMARY OF THE INVENTION

From the above, it will be apparent that a need exists in the art to overcome the above-noted deficiencies of the prior art. It is therefore a primary object of the invention to provide an objective measurement of higher-order aberrations of the eye which provides an accurate estimate for the subjective refraction.

It is another object of the present invention to provide a reliable measurement for multiple pupil sizes, light levels, and ages.

It is yet another object of the invention to determine the metric which best expresses the optimal image for vision.

It is still another object of the invention to provide reliable measurement for a greater percentage of the population.

The above and other objects are achieved through a computational system and method which determine the refractive error of the eye from measurements of its wave aberration. The procedure calculates the combination of sphere and cylinder that optimizes one or more metrics based on the distribution of light in the retinal image, which is affected by the higher-order aberrations. The retinal image, which is the distribution of light on the retinal or image plane, is calculated from the results of a Shack-Hartmann or other detector. A metric based directly on the retinal image can be computed, or a metric which is a proxy for the retinal image can be used. Any metric on the image plane can be used, and one or more metrics can be used. The method yields an optimum image that is correlated with the subjective best retinal image. Since the method is computational, a computer is the only hardware required, and it can be combined with a wavefront sensor in a compact instrument.

The present invention takes into account the fact that while pupil-plane metrics do not accurately predict the subjective refraction, image-plane metrics do. While the techniques of the prior art were adequate for only about 25% of subjects with a precision of ±0.25 D or 50% of subjects with a precision of ±0.5 D, the present invention will provide suitable correction for most subjects Keith errors <0.25 D.

For estimation of the subjective refraction, both the peak and the tails of the metric value can be used; that is, information from the curve of the metric other than the location of the maximum can be used. For example, the width of the curve can be used for "tolerancing," since a narrower curve indicates a lower tolerance and thus a more critical need for accurate correction. An example is better fitting of a contact lens which corrects sphere and not astigmatism for subjects with a large tolerance to astigmatism.

Unlike autorefraction, which is limited to a single pupil size, the present invention is not so limited. The present invention allows the subjective refraction to be calculated for any pupil size equal to or smaller than the pupil size over which the wave aberration was measured.

The present invention is further directed to a second application flowing from the above-noted computational system and method. While spectacles and contact lenses have been successfully used to correct defocus and astigmatism (second-order aberrations), they leave the higher-order aberrations uncorrected. For small pupils, a conventional correction offers a sufficient improvement. However, it has been found that the higher-order aberrations have a significant impact on the retinal image quality in normal eyes for large pupils and also for small pupils in old subjects or in abnormal subjects such as post refractive surgery or keratoconus patients. Indeed, the use of an adaptive optical system has successfully corrected higher-order aberrations and provided normal eyes with supernormal optical quality. Recent developments make viable the idea of implementing supercorrecting procedures. Thus, lathe technology allows the manufacture of contact lenses with nearly any aberration profile, and there is an ongoing effort to refine laser refractive surgery to the point that it can correct other defects besides conventional refractive errors.

While achieving the correction of all of the aberrations is desirable, that implies a customized correction with many degrees of freedom. Moreover, the higher the order of the aberration, the lower the tolerance to mismatch and the greater the accuracy of the correction required to be effective. A tradeoff that accomplishes the reduction of aberrations while implying a relatively simple robust correction implements a customized correction of only a certain set of higher-order aberrations such as, for example, coma and spherical aberration. Coma and spherical aberration are particularly important because those aberrations are the ones with larger values in the human eye and have a large tolerance to decentration. However, the present invention is general and may similarly be implemented to any other set of aberrations.

In short, if it is possible to detect more aberrations than can be corrected, the aberrations to be corrected are selected, or all of the aberrations are corrected partially. For example, if n aberrations can be measured, $m \leq n$ aberrations can be corrected. The present invention permits a determination of the values of the compensation aberrations in the correcting method required to optimize the subject's vision. For example, in some countries it is common to correct for sphere but not astigmatism. The present invention provides an improved way to do so. As another example, since the eye is not stable, residual aberrations cannot be avoided. The present invention minimizes problems caused by such residual aberrations.

Thus, the second part of the present invention provides a computational procedure to design an optimum pattern of a customized correction of a few aberrations of the eye besides astigmatism and defocus. The procedure considers the effect of the remaining aberrations that have been left uncorrected to calculate the adequate values of the aberrations to be corrected in order to achieve the best image quality.

Several metrics can be used to describe retinal image quality. The computational procedure calculates the prescription of the refractive error of a subject based on the optimum values of those metrics.

The present invention is based on the surprising discovery that when correction is carried out in accordance with a metric measured on the image plane, it is not necessary to take into account the brain's preference in image quality. The use of a metric which takes the brain into account produces no significant difference. By contrast, it was originally believed that corrections would have to take into account the brain's preference in image quality. For that reason, techniques from astronomy, in which such effects do not arise, would not have been considered. Thus, computation is significantly simplified over what the inventors originally thought was required.

Higher-order aberrations influence the optimal subjective refraction and the tolerance to miscorrections. Pupil-plane metrics (e.g., wave aberration RMS) do not accurately predict the subjective refraction. Thus, wavefront sensors can improve objective refraction by using image-plane metrics (or quantities which function as proxies for image-plane metrics) to incorporate the effect of higher-order aberrations.

The present invention allows the prediction of subjective refraction from any reliable wavefront device and performs substantially better than current autorefractors. Some limitations of autorefractors are: the pupil size; the level of radiation (often low) returning from the retina and analyzed by the detector; the fact that the target, such as a grating, is blurred twice in its double pass through the eye's optics; and the fact that current autorefractors estimate three and only three parameters (sphere, cylinder and axis). By contrast, the present invention can optimize the correction for any number of aberrations, from defocus alone to as many aberrations as have been measured. The present invention is applicable to any technique for correction, including contact lenses, intraocular lenses, spectacles, laser refractive surgery, and adaptive optics. Further, the present invention allows prescribing a correction based on the patient's tolerance to departures from the optimum correction. For example, the patient's tolerance to a contact lens that corrects only sphere and not astigmatism can be objectively estimated.

With regard to the above-mentioned proxy metric, it has been found empirically that in many subjects, the best image can be predicted from the aberration coefficients. If the aberration coefficients can be used to calculate two results whose errors have opposite signs, the proxy metric can be a simple average or a weighted average.

BRIEF DESCRIPTION OF THE DRAWINGS

A preferred embodiment of the present invention will be set forth in detail with reference to the drawings in which:

FIGS. 1A–1C show examples of image formation by eyes having various degrees of aberration;

FIGS. 1D and 1E show the results of prior-art techniques for vision correction;

FIG. 3 shows a modification of the flow chart of FIG. 2 to take chromatic defocus into account;

FIG. 3A shows a search for an optimum metric in one dimension of three-dimensional space;

FIG. 7 shows an apparatus for implementing the operations of FIG. 2 or FIG. 3;

FIG. 10 shows the dependence of the discrepancy between subjective and objective refraction on the RMS of the wave aberration;

FIG. 11 shows the dependence of tolerance to refractive errors on higher-order aberrations;

DETAILED DESCRIPTION OF THE PREFERRED EMBODIMENTS

Figure 1A:
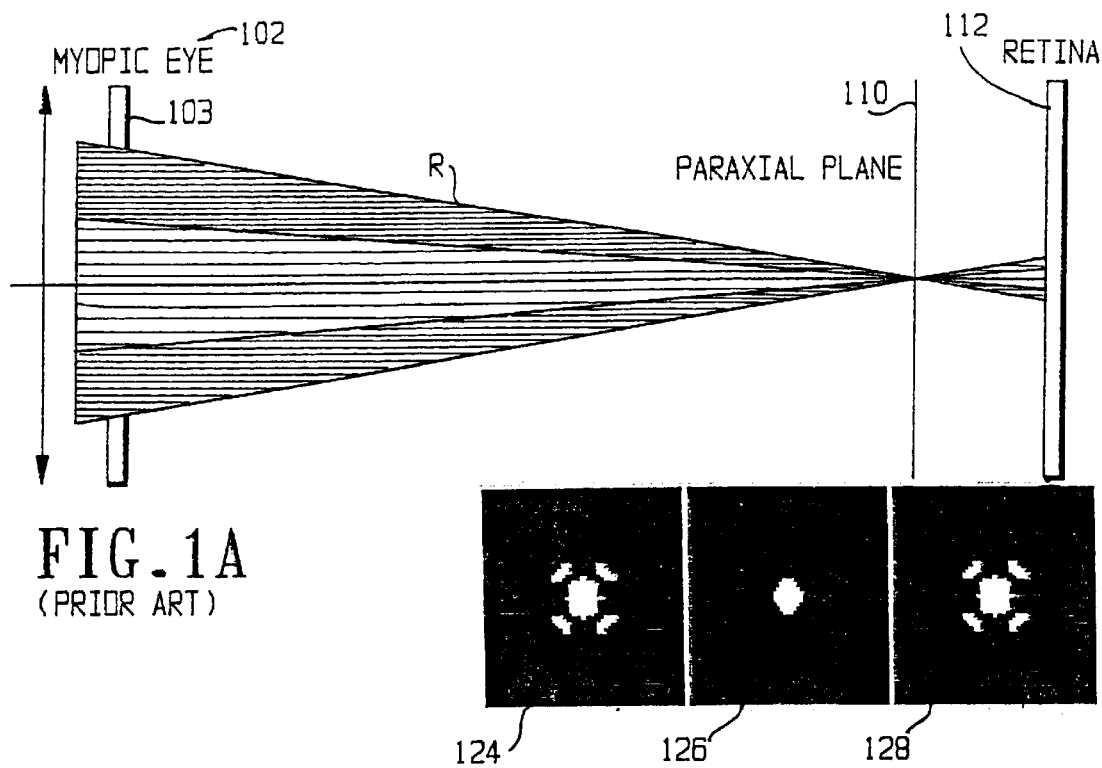
Figure 1B:
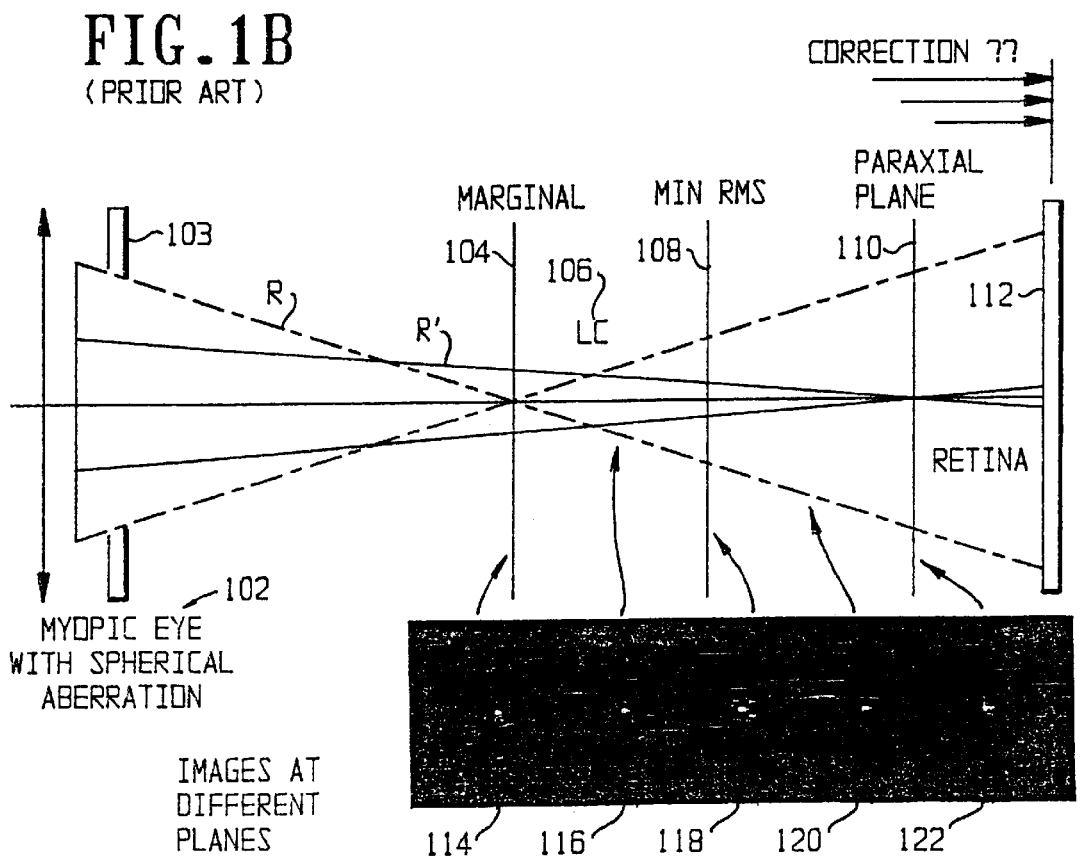
Figure 1E:
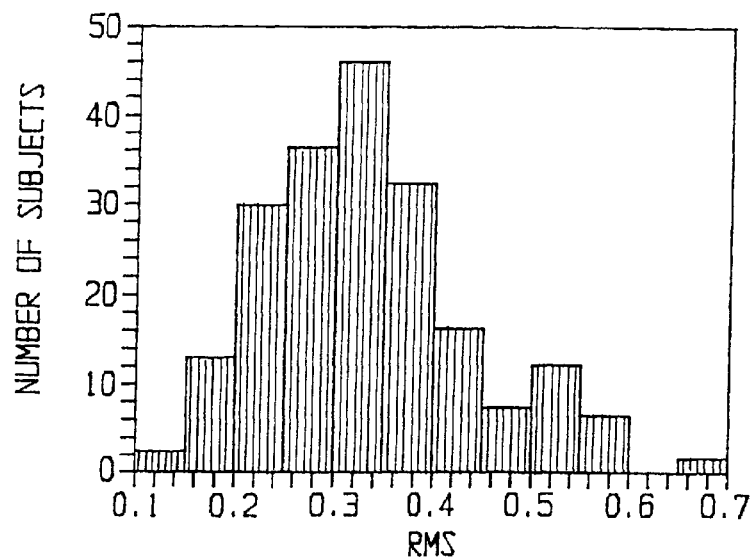

Before the preferred embodiment is described in detail, certain quantities will be defined.

Wave aberration is the difference in optical path between marginal rays and rays passing through the center of the exit pupil. It can be expressed as a linear combination of Zernike polynomials $Z_n^m$:

$$W(\rho, \theta) = \sum_{n,m} a_n^m \cdot Z_n^m(\rho, \theta), \quad (2)$$

where $a_n^m$ are the Zernike coefficients, and $(\rho,\theta)$ is a point at the pupil plane in polar coordinates, $\rho$ being the radial coordinate normalized to the radius of the pupil ($r_0$). The order of the aberration is indicated by n.

Second-order coefficients represent:

$a_0^2$: defocus, $a_2^{\pm 2}$: astigmatism balanced with defocus.

Pupil function is defined as:

$$p(r, \theta) = A(r, \theta) \cdot \exp\left[i \frac{2\pi}{\lambda} W(r, \theta)\right], \quad (3)$$

where $A(r,\theta)$ is the amplitude transmitted through the pupil (which in the preferred embodiment will be assumed to be equal to 1 within the pupil, and 0 outside the pupil), and $W(r,\theta)$ is the wave aberration.

Point spread function (PSF) is the distribution of irradiance on the image plane that the eye forms of a point source. It can be calculated from the pupil function by means of a Fourier transform (FT):

$$PSF(x,y)=|FT(p(\lambda d\eta, \lambda d\xi)|^2, \quad (4)$$

where d is distance from the pupil to the image plane, (x,y) are Cartesian coordinates on the image plane, and $(\eta,\xi)$ are Cartesian coordinates on the pupil.

Modulation transfer function (MTF) is the modulus of the so-called optical transfer function (OTF) which is the Fourier transform of the PSF. Thus:

$$MTF(f_x, f_y)=|FT(PSF(x, y))|^2, \quad (5)$$

where $(f_x, f_y)$ are spatial frequencies. The MTF yields the relation between the contrast of the object and the associated retinal image at every spatial frequency, and it incorporates only the effects of the optic of the eye.

Neural contrast sensitivity function (NCSF): Both optical and neural factors affect the visual performance. The contrast sensitivity of the visual system to interference fringes provides an estimate of the contrast sensitivity of the retina and the brain alone.

Contrast sensitivity function (CSF) is the standard measurement of how sensitive observers are to gratings with different spatial frequencies. Since both optical factors and neural factors are implicated, the CSF is ultimately a description of the visual performance of the subject. For example, the maximum spatial frequency that can be detected (i.e., when the CSF falls to zero) gives a measure of the observer's visual acuity.

The CSF can be determined subjectively by finding the lowest contrast (threshold) at which the observer can detect a sinusoidal grating of a particular spatial frequency. The reciprocal of the threshold is the CSF. Objectively, the CSF can be obtained as the product of the optical modulation transfer function and the neural contrast sensitivity:

$$CSF(f_x, f_y)=MTF(f_x, f_y) \cdot NCSF(f_x, f_y). \quad (6)$$

Strehl ratio is the peak value of the PSF or, equivalently, the volume or energy of the MTF.

Variance of the PSF measures the difference between the lowest values of the PSF and the highest values. The larger the variance, the sharper the PSF. It is calculated mathematically as:

$$\text{var}(PSF)=<PSF^2>-<PSF>^2, \quad (7)$$

where <...> indicates the mean value.

Entropy of the PSF: The entropy of an image is a measure of how spread the irradiance is from the center; i.e., it is a measure of the effective area of the image. The entropy of the PSF is calculated as:

$$\text{Entropy} = -\sum_{n,m} PSF(n, m) \cdot \log PSF(n, m). \tag{8}$$

The aberration-free PSF (Airy image) possesses the minimum entropy. Any aberration leads to increased entropy.

Encircled energy (within Airy disk) of the PSF. The encircled energy that falls within a small area around the peak of the image can solve the potential problem with the Strehl ratio, since it would measure the intensity integrated in an region rather than the single peak of intensity. A convenient metric is the encircled energy calculated as the fraction of light in the PSF that falls within an area corresponding to the Airy disk. The Airy disk encircles 84% of the total energy in the PSF. The encircled energy could be implemented with a disk encircling more or less of the total energy, as various circumstances warrant.

The derivation of the sphere and cylinder from the aberration coefficients will now be described. Let W be a wave aberration, in the Seidel form, describing a lens that corrects defocus and astigmatism:

$$W = A_d \rho^2 + A_a \rho^2 \cos(\theta - \theta_a), \tag{9}$$

where $\theta_a$ indicates the axis of the astigmatism. The sphere (S) and cylinder (C), in diopters, of the correcting lens are:

$$S = -\frac{2}{r_0^2} A_d, \quad C = -\frac{2}{r_0^2} A_a, \tag{10}$$

where $r_0$ is the radius of the pupil that the wave aberration describes.

If the wave aberration of the lens is expressed in Zernike polynomials, the wave aberration is:

$$W = a_2^0 \cdot Z_2^0 + a_2^2 \cdot Z_2^2 + a_2^{-2} \cdot Z_2^{-2}. \tag{11}$$

The relationship between the Zernike coefficients and the Seidel coefficients is:

$$A_a = 2\sqrt{6}\sqrt{(a_2^{-2})^2}, A_d = 2\sqrt{3}a_0^2 - A_a/2, \tag{12}$$

with the axis given by $$\theta_a = \frac{1}{2} \arctan \frac{a_2^{-2}}{a_2^2}.$$

Five different image quality metrics are used in the preferred embodiment: Strehl ratio; entropy of the PSF; variance of the PSF; MTFa, defined as the integral of the MTF within the range of discriminable frequencies, from 0 to 60 c/deg; and CSFa, defined as the integral of the CSF, which is obtained as the product of the MTF and the neural CSF. All of them are divided by the maximum (minimum for entropy) value corresponding to the diffraction limit, so that they are normalized to a maximum (minimum for entropy) value of 1 for the aberration-free case.

Figure 2:
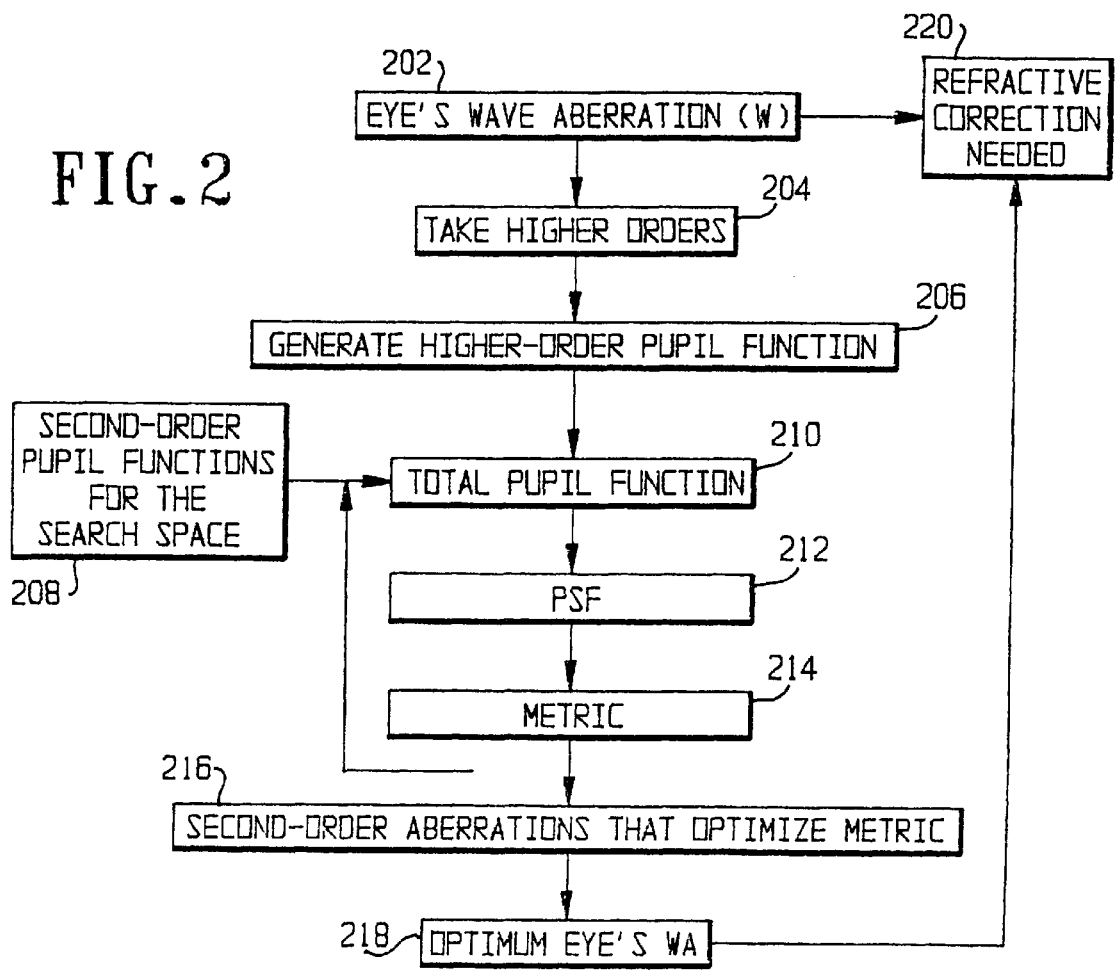
FIG. 2 shows a flow chart of operations performed in determining a refractive correction needed, assuming monochromatic light.

Next, the steps of the procedure to estimate the refraction of the eye from wave aberration measurements will be described. For the sake of clarity, the method will first be disclosed assuming monochromatic light and next for polychromatic light. The flow charts of FIGS. 2 and 3 summarize the steps of the algorithm for the monochromatic and polychromatic cases, respectively.

1. The wave aberration (W) of the eye expressed in Zernike polynomials in step 202 is the input data. Let $\lambda_0$ be the wavelength for which that wave aberration has been measured. From W we extract the second-order Zernike coefficients, $a_2^{0,\pm 2}$, in step 204, yielding a "higher-order wave aberration":

$$W_{h-o} = \sum_{n>2} a_n^m \cdot Z_n^m. \tag{13}$$

$W_{h-o}$ is composed of higher-order aberrations, some of which are balanced with defocus and astigmatism in the sense of minimum RMS. If the minimum RMS corresponded to the best image, the refractive correction of the eye would be obtained directly from the coefficients $a_2^{0,\pm 2}$. In general, that wave aberration will not represent the optimum state of the eye after a refractive correction, which is the ultimate goal. However, it constitutes a reasonable first approximation from which we can begin the search of the additional amount of defocus and astigmatism required.

2. Construction of a "higher-order pupil function," $p_{h-o}$, from $W_{h-o}$, by means of Eq. (3) in step 206. That pupil function characterizes the higher-order aberrations of the subject and does not need to be calculated anymore.

3. Construction of pupil functions for second-order wave aberrations consisting of combinations of defocus and astigmatism within the space of search in step 208. Those wave aberrations are of the form:

$$W_{s-o} = c_2^0 Z_2^0 + c_2^2 Z_2^2 + c_2^{-2} Z_2^{-2}, \tag{14}$$

where the coefficients $c_2^{0,\pm 2}$ cover the space of search.

The pupil functions are then:

$$p_{s-o} = A \cdot \exp\left[i \frac{2\pi}{\lambda_o} W_{s-o}\right]. \tag{15}$$

Those pupil functions are independent of the subject. They can thus be calculated once and stored to be used anytime, thereby enhancing computational efficiency.

An important question is how large and dense should be the space of the parameters $c_2^{0,\pm 2}$ where we want to find the optimum set of defocus and astigmatism. Fortunately, that set can be found at a finite distance and not far from the origin. Actually, the amount of second-order aberrations that produce a better image quality in the presence of higher-order aberrations is limited by the magnitude of such higher-order aberrations. Beyond a limit the image quality progressively deteriorates. A reasonable choice is a range of values limited by the longest distance between any pariaxial ray and any marginal ray. The interval of search can be twice that value to make sure the optimum set will fall within our space of search.

The sampling of the space of search can be determined from the minimum step difference in focus that a subject can detect. A spacing of 0.1 microns between values of the Zernike coefficients $c_2^{0,\pm 2}$ is adequate. For example, for a 4 mm pupil, that step corresponds to 0.17 diopters (see Eqs. (10–12)).

4. Construction of "total pupil functions" in step 210 as the product of the higher-order pupil function, $p_{h-o}$, and every second-order pupil function that cover the space of search, $p_{s-o}$:

$$p_{total} = p_{h-o} \cdot p_{s-o}. \tag{16}$$

5. Calculation of the point spread function (PSF) with Eq. (4) in step 212.

6. Calculation of the metrics of image quality as explained above in step 214.

7. Selection of the parameters $c_2^{0,\pm 2}$ which give the optimum values for the metrics in step 216.

The space of search is typically a three-dimensional space, i.e., defocus, astigmatism and axis of astigmatism. FIG. 3A shows the metric value plotted against one dimension, namely, defocus. A small error between the maximum of the metric and the subjectively determined optimum correction would indicate that the metric is a good predictor of subjective refraction.

8. Determination of the refraction of the subject. The optimum wave aberration of the eye after correcting defocus and astigmatism, as determined in step 218, should be:

$$W_{optimum} = c_0^2 \cdot Z_0^2 + C_2^2 + c_2^{-2} \cdot Z^{2-2} + W_{h-o}. \quad (17)$$

Since the original wave aberration of the eye is W, we have:

$$W = W_{lens} + W_{optimum}. \quad (18)$$

Equations (17) and (18) show that we have to correct the eye with a lens whose wave aberrations are $$W_{lens} = (c_0^2 - a_0^2) \cdot Z_0^2 + (c_2^2 - a_2^2) \cdot Z_2^2 + (c^{2-2} - a_2^{-2}) \cdot Z_2^{-2}. \quad (19)$$

Therefore, the refraction of the subject as determined in step 220 will be:

$$S = -\frac{2}{r_0^2} 2\sqrt{3}\,(c_2^0 - a_2^0) - C/2, \quad (20)$$

$$C = -\frac{2}{r_0^2} 2\sqrt{6}\,\sqrt{(c_2^2 - a_2^2)^2 + (c_2^{-2} - a_2^{-2})^2},$$

with the axis of the cylinder being:

$$axis = \frac{1}{2}\arctg\frac{(c_2^{-2} - a_2^{-2})}{(c_2^2 - a_2^2)}.$$

Note that if the minimum RMS had corresponded with the best image, then the search would yield $c_2^{0,\pm 2}=0$, and the refraction would be directly calculated from the original coefficients $a_2^{0,\pm 2}$.

Figure 4:
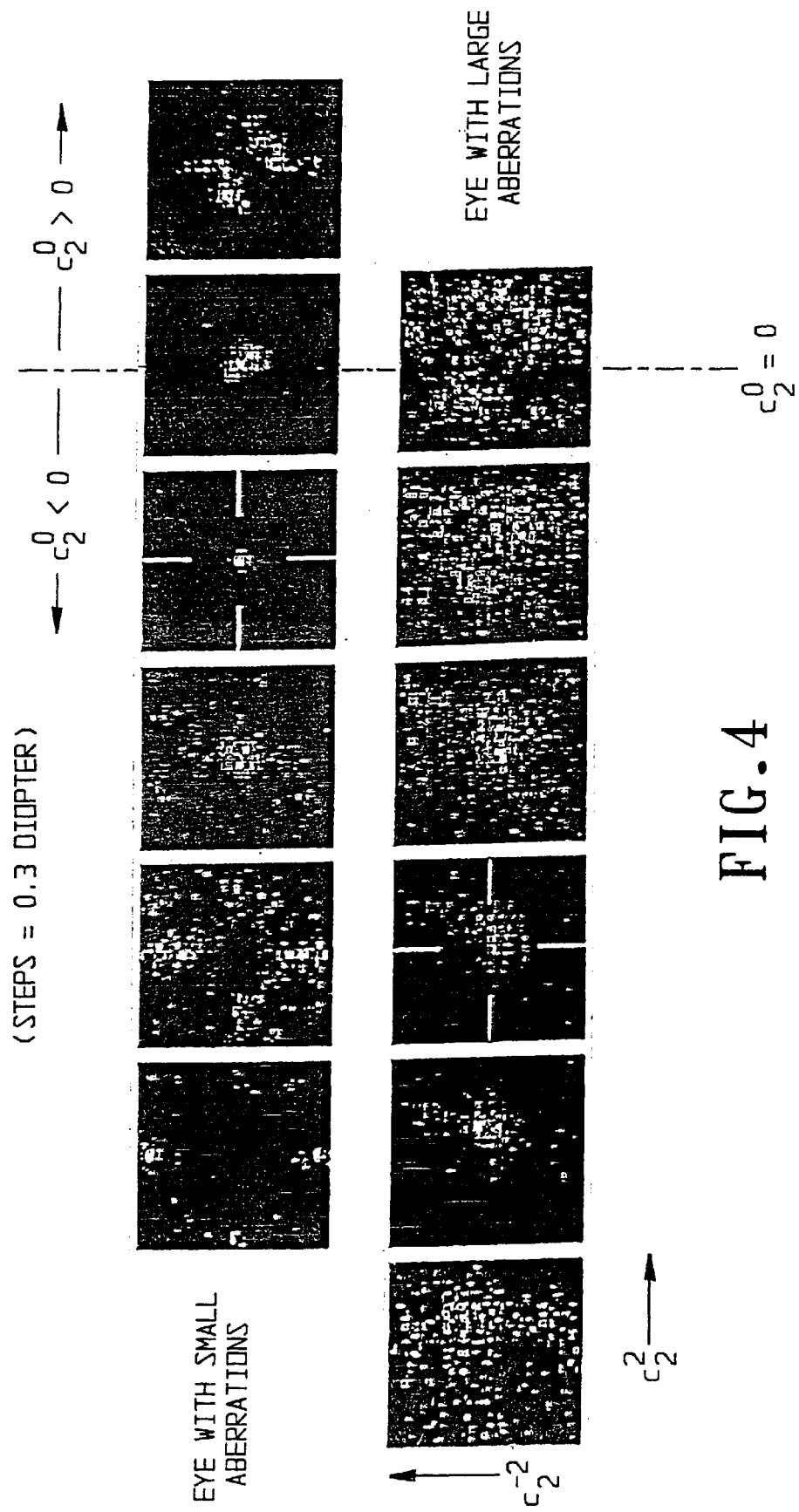
FIG. 4 shows examples of the parameter search of FIG. 2 for an eye with small aberrations and an eye with large aberrations.

FIG. 4 shows an example of the search for parameters $c_2^{0,\pm 2}$ for two eyes with different amount of aberrations. The gray level indicates the value of one of the metrics of image quality. For the less aberrated eye, the maximum value of the metric is obtained for a position very close to the minimum RMS condition ($c_2^{\pm 2}\sim 0$ and a small value of $c_2^0$). However, for the more aberrated eye, it is necessary to introduce an extra value of astigmatism and defocus.

Since ocular refractive errors are usually corrected to see the broad band illumination that is characteristic of everyday visual scenes, the search of parameters should be made in polychromatic light. The following steps must be implemented in addition to those previously described.

9. Construction of "chromatic pupil functions" (steps 205, 206') as:

$$p_{chro} = A \cdot \exp\left[i\frac{2\pi}{\lambda}c_{chro}Z_2^0\right], \quad (21)$$

where $c_{chro}$ is the Zernike coefficient that represents the defocus for every wavelength, and $\lambda$ is the wavelength taking values within the visible spectrum. The reference wavelength for free chromatic aberration is 555 nm, coincident with the maximum of photopic sensitivity.

10. Calculation of the monochromatic PSF for every wavelength from the "total pupil function," $p_{total}$, and the chromatic pupil functions," $p_{chro}$, in step 212'. The polychromatic PSF is calculated by integrating the monochromatic PSF across the spectral distribution weighted with the standard spectral sensitivity, $V(\lambda)$, of the eye.

11. From the polychromatic PSF, the previous steps are the same to calculate the refraction from the set of coefficients that optimize the metrics. The only exception is that the Zernike coefficient, $a_2^0$, of the original wave aberration must be shifted according to the difference in focus between the reference wavelength and the wavelength for which the aberrations are measured.

Figures 5, 9:
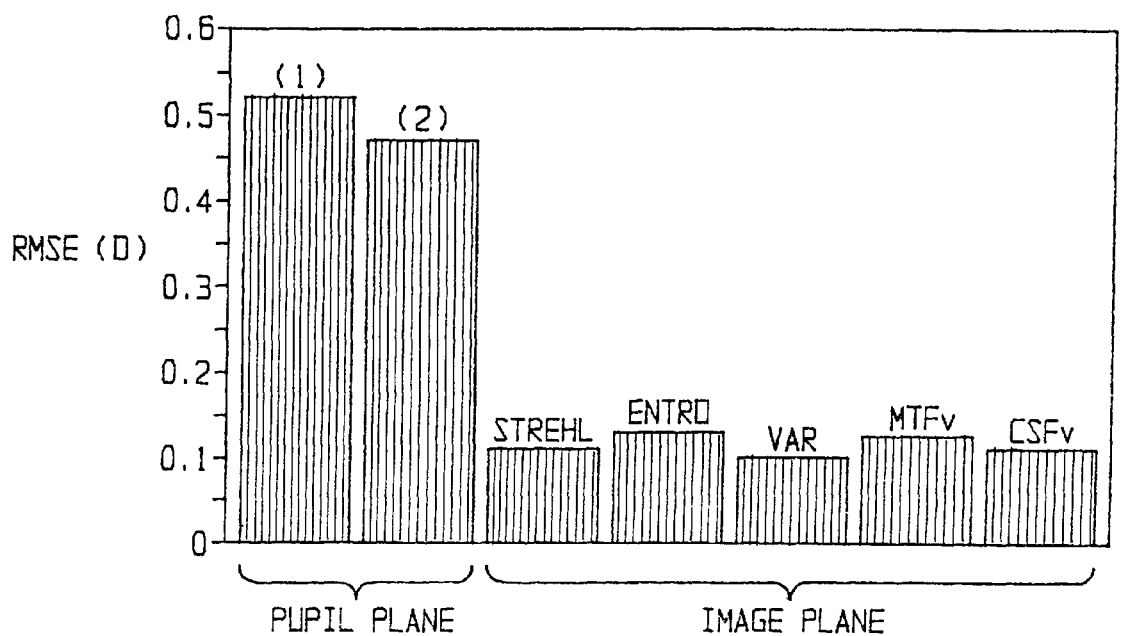
FIG. 5 shows an example of the calculation of an optimal aberration for a subject using the technique of FIG. 3.
FIG. 9 shows the root mean square error (RMSE) of residual refraction after correction through the use of various image metrics.

FIG. 5 shows an example in a subject. From the original wave aberration of the eye we calculated the optimum wave aberration after a compensation of defocus and astigmatism. The sphere and cylinder of the correcting lens prescribed for that eye are obtained.

An extension of the procedure outlined consists of doing a search of the best parameters to implement a customized correction of a few higher-order aberrations besides astigmatism and defocus. As an example, if one can make an aspherical contact lens to correct the spherical aberration of the eye, our procedure can yield the optimum value of aberration that the lens should correct in order to achieve the best image quality in the presence of the uncorrected aberrations.

All the steps described above continue the same by replacing the set of coefficients for defocus and astigmatism by the set of coefficients of all the aberrations that will be corrected.

Figure 6A:
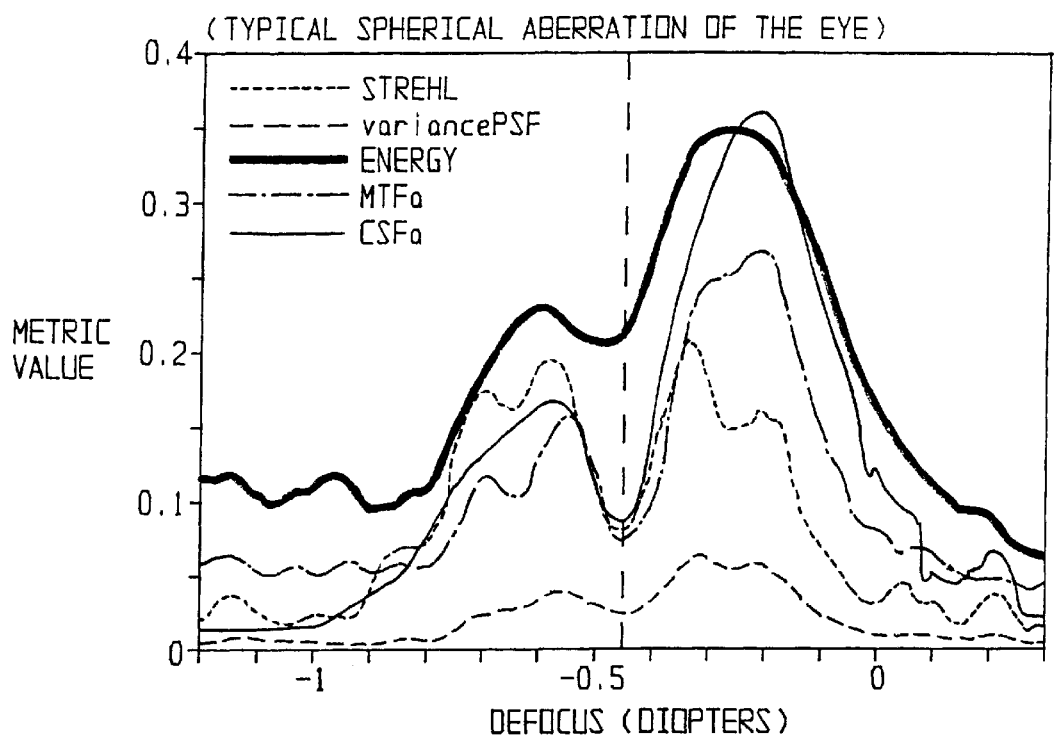
FIGS. 6A and 6B show the values of different metrics at different image planes.
Figure 6B:
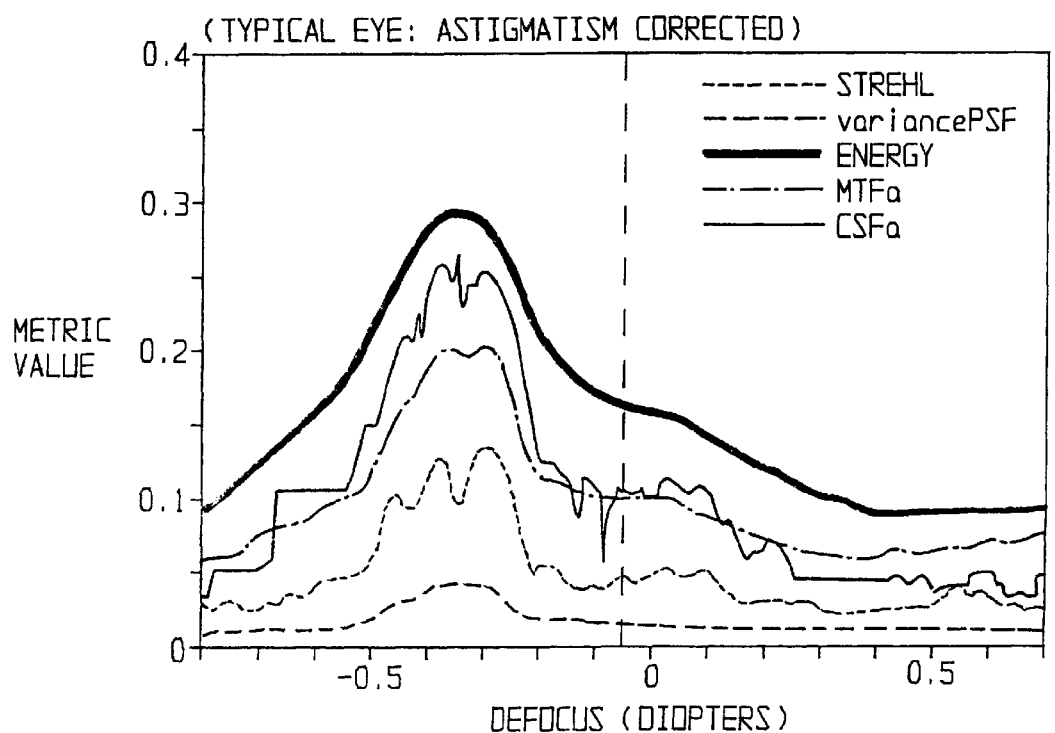

FIGS. 6A and 6B show the value of the different metrics at different image planes. The plane of 0 diopters is the paraxial plane. The vertical dashed line indicates the plane of the RMS minimum. Two examples are shown, one with only spherical aberration (the value for the average eye) in FIG. 6A, and other with all the higher-order aberrations of a typical eye in FIG. 6B. In the case shown in FIG. 6B, the astigmatism has been optimized, and only the dependence on defocus is shown. The following can be observed:

Because of the higher-order aberrations, some defocus is necessary to achieve a best image.

The minimum RMS does not correspond to the maximum of the other metrics.

For the eye with only spherical aberration, one can see that the Strehl ratio exhibits two global maxima symmetrically around the plane of minimum RMS. However, in an eye with all the aberrations, the behavior of the Strehl ratio is more robust.

All the metrics correlate quite well.

Encircled energy, MTFa, and CSFa are the most robust metrics. In addition, they present sharper maxima, which means a more accurate determination of the best image.

FIG. 7 shows an experimental system to measure the subjective refraction and the wave aberration of the subject. The apparatus is based on a Shack-Hartmann sensor, which is well known in the art. The subject sees through the system a Snellen chart presented on a CRT. The subjective refraction and the wave aberration measurements are performed under the same conditions.

More specifically, in the system 700 of FIG. 7, the subject is shown a Snellen chart 702 on a CRT, an LCD screen, or a similar device. Alternatively, the Snellen chart can be printed, or another chart can be used. The Snellen chart 702 is imaged through a beamsplitter 704, a conjugate lens system 706, another beamsplitter 708, and optionally a removable sphere-cylindrical correction system 710 onto the retina of the subject's eye E. Light from a laser diode 712 is directed through the beamsplitter 708 onto the retina of the subject's eye E. The light from the laser diode 712 reflected from the retina passes through the beamsplitter 708, the conjugate lens system 706 and the beamsplitter 704 into a Shack-Hartmann sensor 714, which includes a lenticular array 716 and a CCD or other photodetector array 718. The Shack-Hartmann sensor 714 produces an output which is directed to a computer 720 programmed to perform the technique of FIG. 2 or FIG. 3. A widely-available Pentium III-class computer suffices. The computer 720 outputs the optimal wave aberration of FIG. 2 or 3, step 218, and the required refractive correction of FIG. 2 or 3, step 220. The latter can be supplied to a lens fabrication, surgical correction, adaptive optics, or image simulation system 722, which can prepare a spectacle lens, a contact lens, or an intraocular lens to correct the eye's wave aberration, control a surgical technique upon the eye E to correct the aberration, provide adaptive optics such as a deformable mirror to provide a counter-aberration, or simulate an image showing how the subject would view a scene after correction of aberrations. The last will be explained below with reference to FIGS. 14A–14C.

The refraction and the aberrations were measured in 6 eyes. From the wave aberration, the objective refraction was calculated with the computational procedure maximizing the different metrics.

Figure 8A:
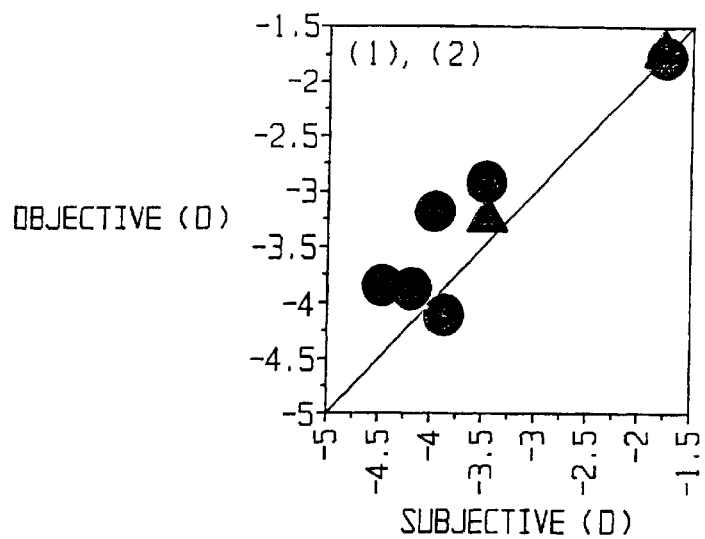
FIGS. 8A–8F show a comparison of subjective and objective refraction as determined through various image metrics.
Figure 8B:
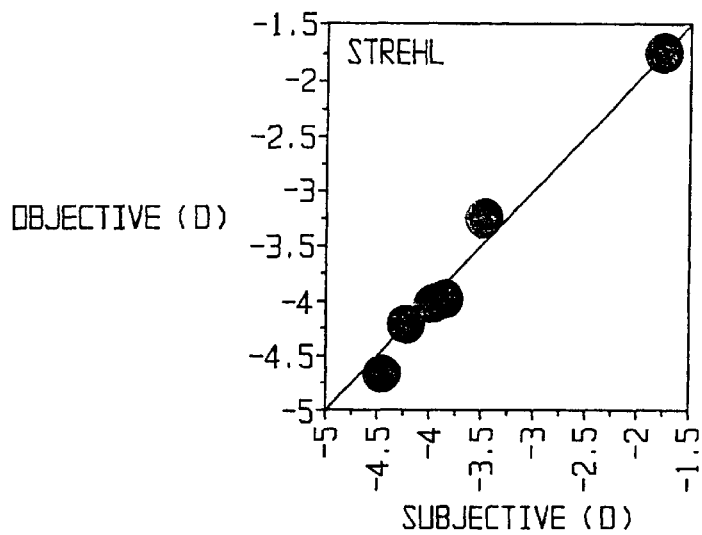
Figure 8C:
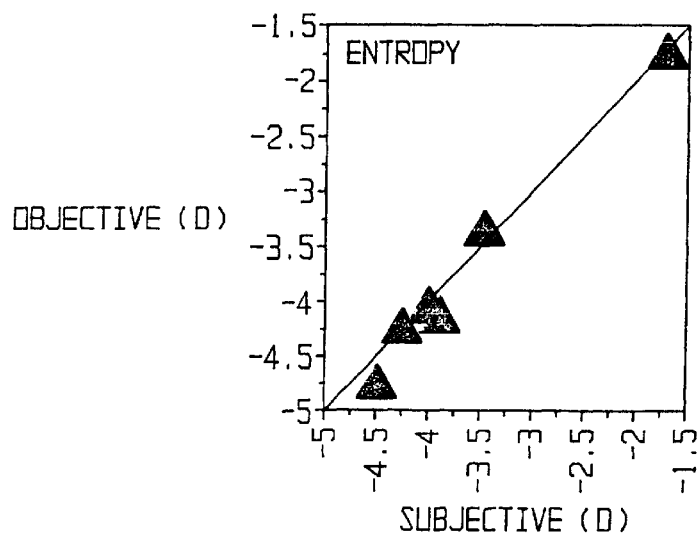
Figure 8D:
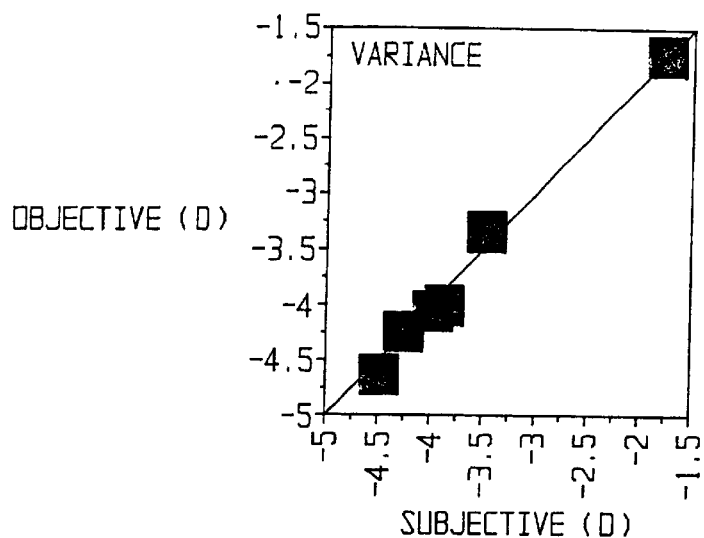
Figure 8E:
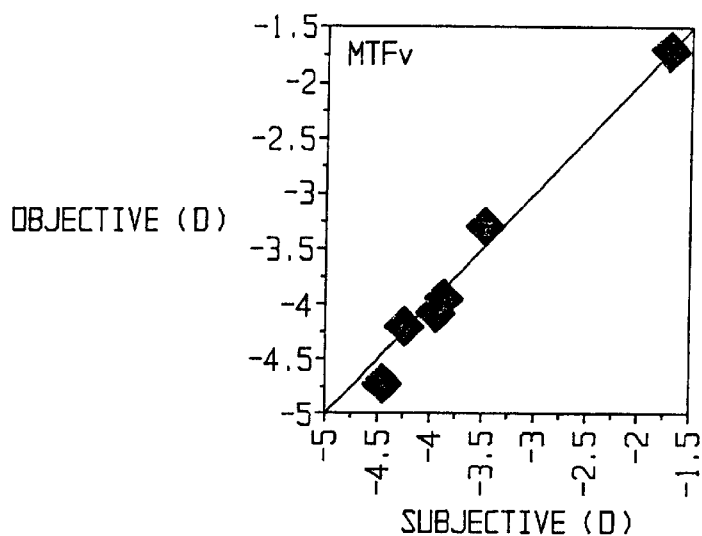
Figure 8F:
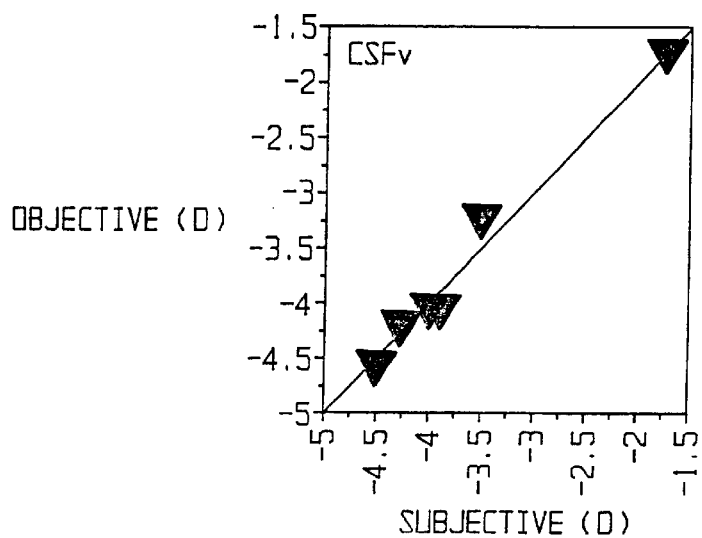

FIGS. 8A–8F show the comparison of the subjective refraction with the estimated =objective refraction for the 6 eyes. FIG. 8A shows the refraction calculated by the RMS and paraxial approximations. FIGS. 8B–8F show the refraction calculated by using the following metrics: Strehl ratio, entropy of the PSF, variance of the PSF, area of the MTF between 0 and 60 c/deg, and area of the CSF. The refraction is expressed in diopters.

The figures show that any of the five metrics of the preferred embodiment will give results much better than those of FIG. 8A. The prediction of the subjective refraction with all of our metrics is good and very similar. The minimum RMS and the paraxial approximation are not good candidates.

FIG. 9 shows the RMSE (root mean square error) of the residual refraction. That is a measure of the average error, in the 6 subjects, between the objective and the subjective refraction. The error in the estimation of the refraction with our procedure is lower than the experimental error that the subjective refraction is performed for (usually 0.25 diopters). Also, FIG. 9 confirms the observation made with reference to FIGS. 8A–8F that the five metrics of the preferred embodiment give much better results than either the RMS technique (1) or the paraxial technique (2).

FIG. 10 shows the dependence of the discrepancy between the subjective and the objective refraction shown in FIGS. 8A–8F, on the RMS of the wave aberration. In the RMS of the wave aberration only the higher-order aberrations (not defocus and astigmatism) are included. As the amount of higher-order aberration increases, the error increases for the paraxial or the minimum RMS approximations. The error in the refraction estimated with the other metrics shows no dependence with the amount of higher-order aberrations.

FIG. 11 shows that higher-order aberrations also influence the eye's tolerance to refractive errors. That figure shows curves of a metric value against refractive error in diopters for two eyes. The curve for eye 1 shows a much greater slope from its peak, and thus a lower intolerance to refractive errors, than the curve for eye 2.

Figure 12A:
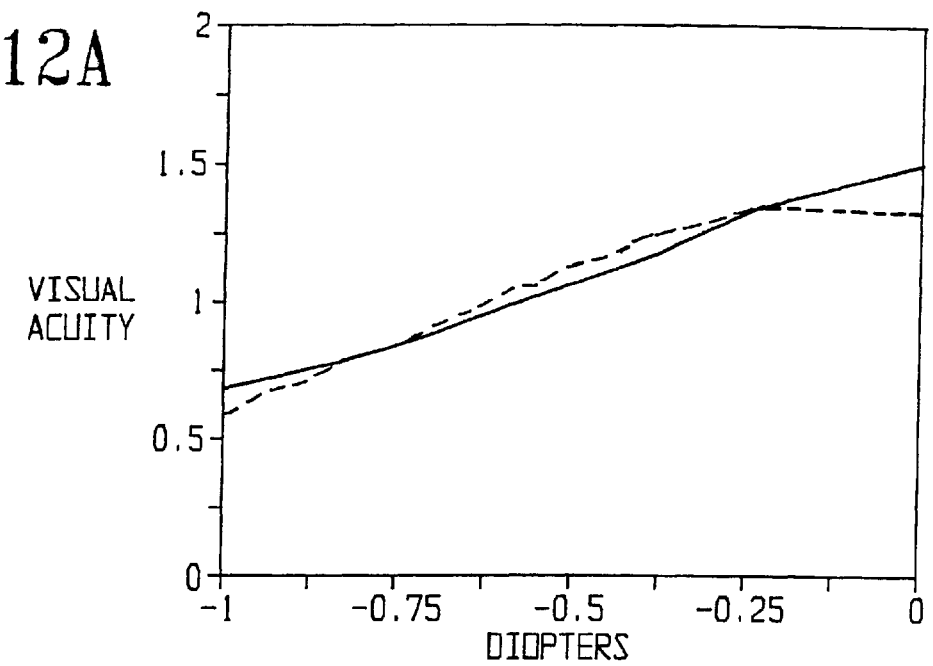
FIGS. 12A and 12B show a comparison between metric tolerance and subjective acuity tolerance.
Figure 12B:
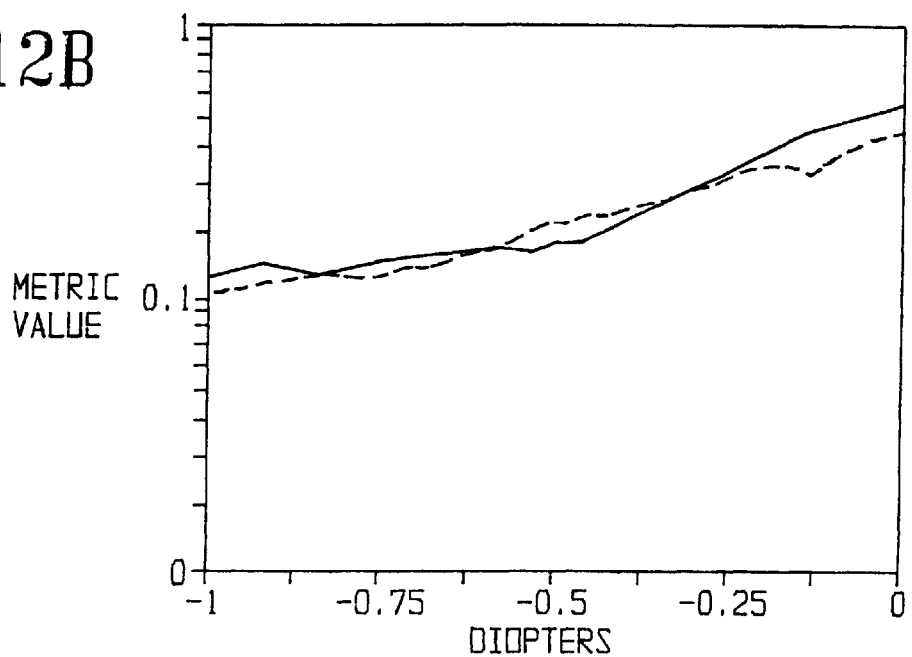

FIGS. 12A and 12B show metric tolerance curves plotted along with subjective acuity tolerance for two eyes. As shown, the two types of tolerances follow each other closely.

From the above, it will be seen that even when not all measured aberrations can be corrected, or when the measured aberrations can be corrected only partially, the tolerances provide a way to determine which corrections will be the most effective. For instance, with reference to FIG. 11, if the aberrations in eye 1 are corrected to bring the curve down to that of eye 2, then the variation in the metric will be greatly reduced, and failure to correct the remaining aberrations will have a much smaller effect on the subject's vision. Tolerancing is an example of a general principle of the present invention, namely, that if more aberrations can be measured than corrected, the correction is done which gives the best improvement in vision.

Figure 13A:
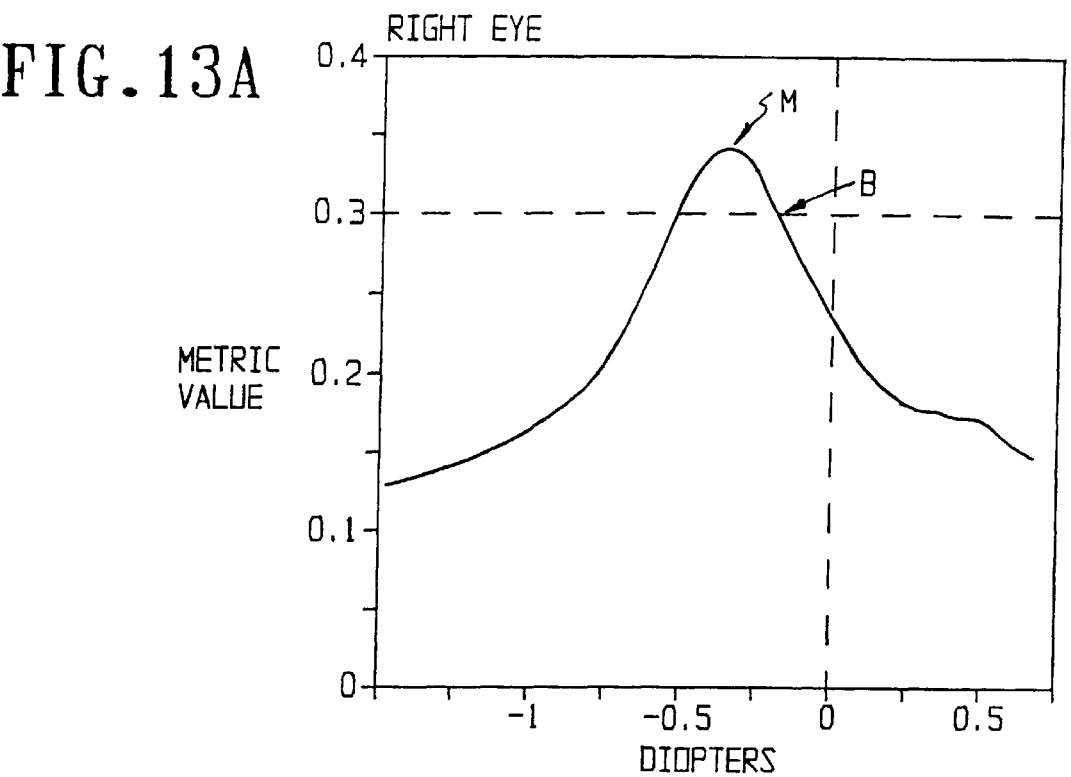
FIGS. 13A and 13B show binocular refraction correction.
Figure 13B:
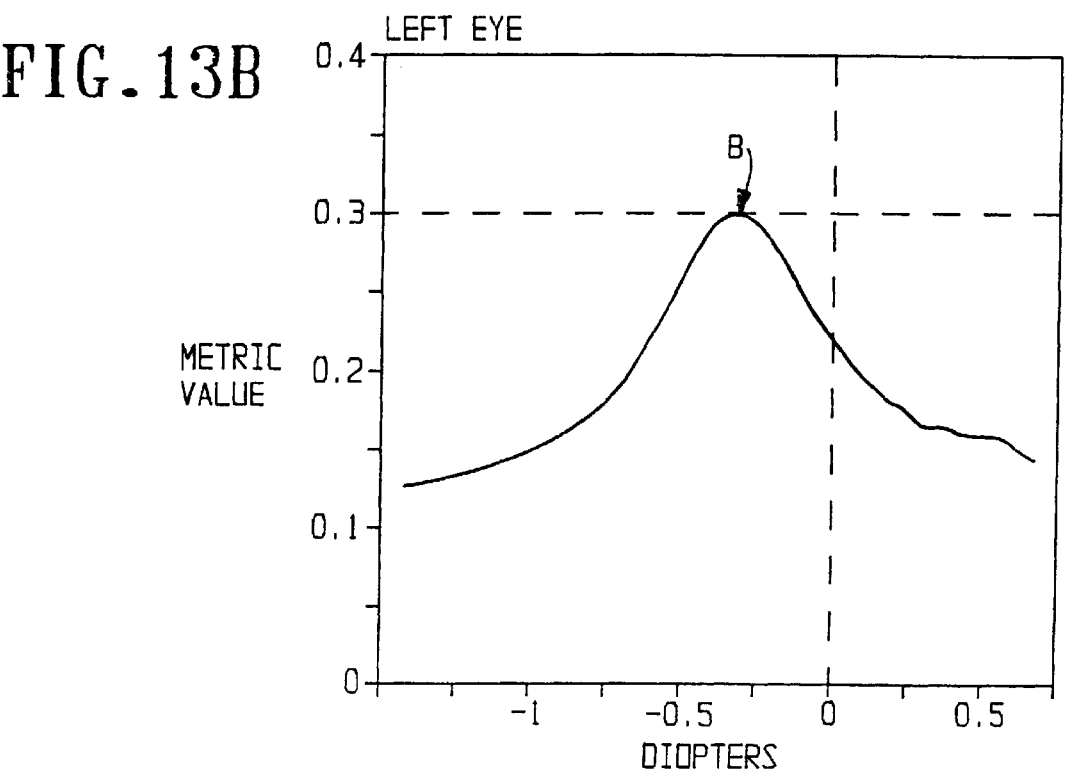

Binocular balancing will now be explained with reference to FIGS. 13A and 13B, which show curves of a metric value plotted against diopters for the right and left eyes, respectively. The arrow marked M indicates the best monocular correction for the right eye, while the arrow marked B indicates the best binocular correction based on a balance with the worse of the two eyes.

Binocular balancing takes into account the different needs of different subjects. For example, if two subjects have identical vision, but one requires near vision (e.g., works in front of a computer all day), while the other one requires far vision (e.g., drives a truck for a living), they should not have the same eyeglass prescription. In binocular balancing, the best refraction at infinity is chosen at first, and then the refraction is adjusted in accordance with the subject's actual working conditions. That is, binocular balancing determines how successful correction will be over a range of distances (depth of field) other than infinity.

The preferred embodiment has so far been described in terms of the calculation and use of actual image-plane metrics. However, any metric which is a proxy for an image-plane metric, i.e., which reflects the quality of the image on the image plane, can be used. For example, while the conventional RMS and paraxial techniques described above are by themselves unsuitable, they err in the opposite directions and therefore can be averaged. The average can be a simple average (50%—50%) or a weighted average. The average is a proxy for the quality of the image on the image plane, which neither the RMS technique nor the paraxial technique could provide on its own.

The objective procedure described yields an accurate value for the subjective refraction of the subject. It seems that the different image quality metrics proposed produce similar results. However, some of them, as for example the CSF, could perform a more robust role, since they present single peaks and narrower windows of tolerance.

The curves of tolerance described above indicate that the present invention can be implemented to be an intelligent method to prescribe a customized ocular refraction considering several factors such as accepted tolerance, the subject's working conditions, pupil diameter, etc.

Figure 14A:
FIGS. 14A–14C show simulated images of a scene viewed by a subject after various types of correction.
Figure 14B:
Figure 14C:

Another practical application will be disclosed with reference to FIGS. 14A–14C. The optimization of an image metric allows not only an estimation of the subjective refraction, but also a simulation of scenes that the subject would see after a best correction. Simulated images are often used to see how the subject sees the real image with aberrations. Usually these simulated images are calculated by using pupil plane methods, so that they do not truly correspond to the actual images that the observer sees.

An example is set forth in FIGS. 14A–14C. The aberrations of a typical eye were used to calculate the image of a scene through the eye's optics when the eye is best corrected for defocus and astigmatism. FIG. 14B shows a simulated image assuming optimization of image-plane metrics, while FIGS. 14A and 14C show simulated images assuming optimization of pupil-plane metrics by the paraxial approximation and minimum RMS, respectively. A comparison of FIG. 14B with FIGS. 14A and 14C shows that the optimization of image-plane metrics produces the least blurred image.

Images can be simulated after a best correction, whether the correction is for defocus and astigmatism, for defocus only, or for any set of aberrations. The simulation of images would be an important complementary feature in an instrument. Depending on the particular aberrations of each subject, the retinal images may be very different, and it is very important to have an estimation of those images when one is going to apply a correction. Just an example: if the simulated images correcting and not correcting the astigmatism of an eye are similar in appearance, that would indicate that the correction will not provide much benefit.

It will be readily apparent from the above that the present invention provides an advantage over the prior art in terms of reliable measurement. However, to demonstrate further the advantages of the present invention, experimental results will now be presented for a larger patient population, in which a preferred embodiment of the present invention is compared with some alternative approaches.

The wave aberrations of 146 eyes were analyzed to determine which of three methods to objectively estimate the subjective refraction most closely matches subjective refraction measurements. The three methods were:

WF rms prediction, a method based on the pupil plane that uses the aberration coefficients analytically to minimize the rms of the wave aberration;

AUTO, which corresponds to measurements with a commercially available autorefractor; and OPT, a method within the present invention which involves maximizing the retinal image quality by finding the values of defocus and astigmatism for which an image quality metric is optimized in the presence of the higher order aberrations. In particular, the experimental results set forth below were calculated by optimizing the entropy of the PSF.

Figure 15A:
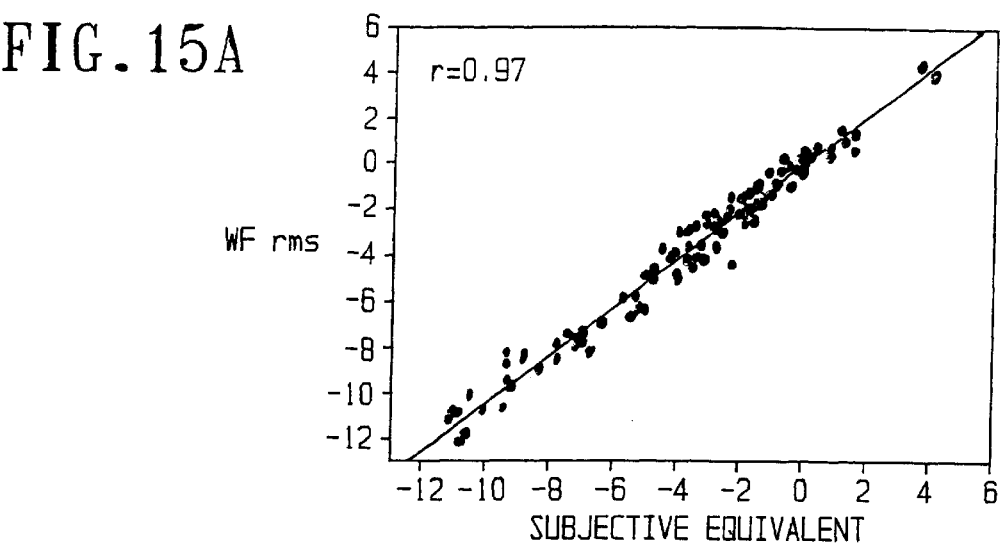
FIGS. 15A–15C show the correlation between the subjective spherical equivalent and the objective spherical equivalent according to experimental results taken with a preferred embodiment of the present invention and with two other techniques.
Figure 15B:
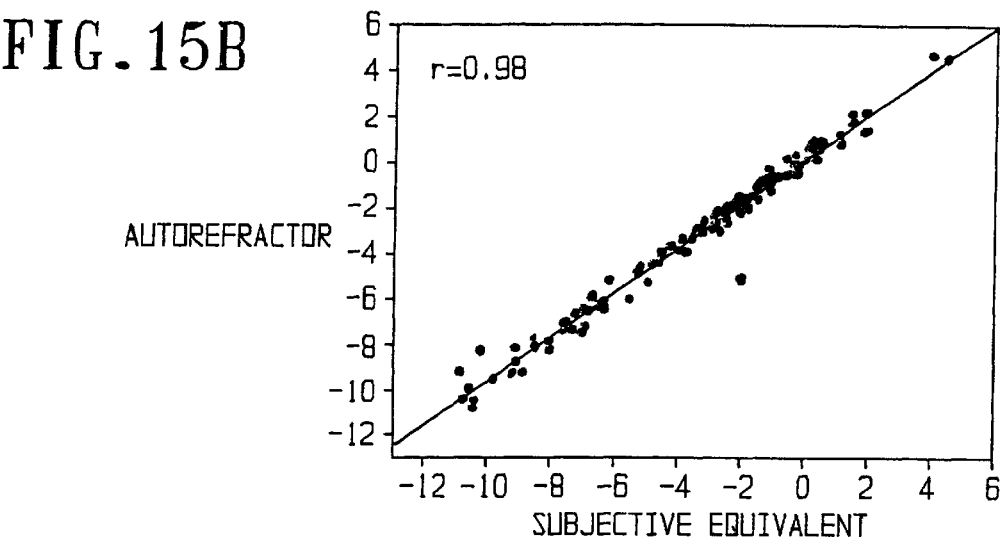
Figure 15C:
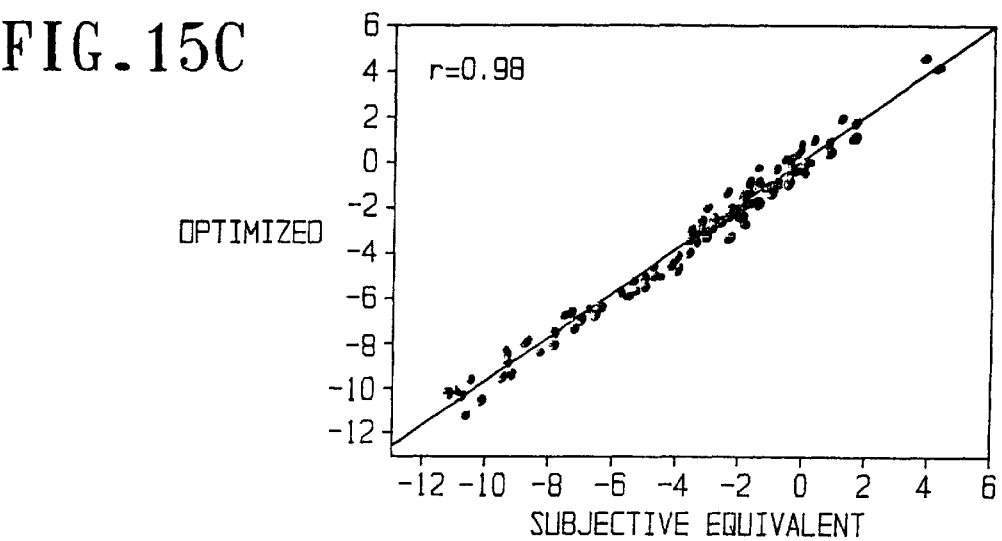

FIGS. 15A–15C show the correlation between subjective spherical equivalent and the objective spherical equivalent from WF, AUTO, and optimization (OPT), respectively, in diopters. All show a correlation coefficient close to one.

Figure 16A:
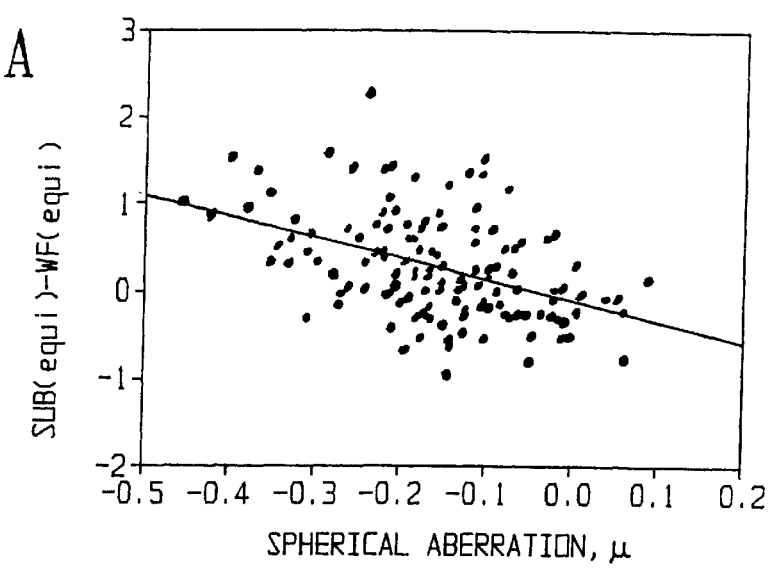
FIGS. 16A–16C show the error between subjective and objective spherical equivalent as a function of the spherical aberration for the same experimental results.
Figure 16B:
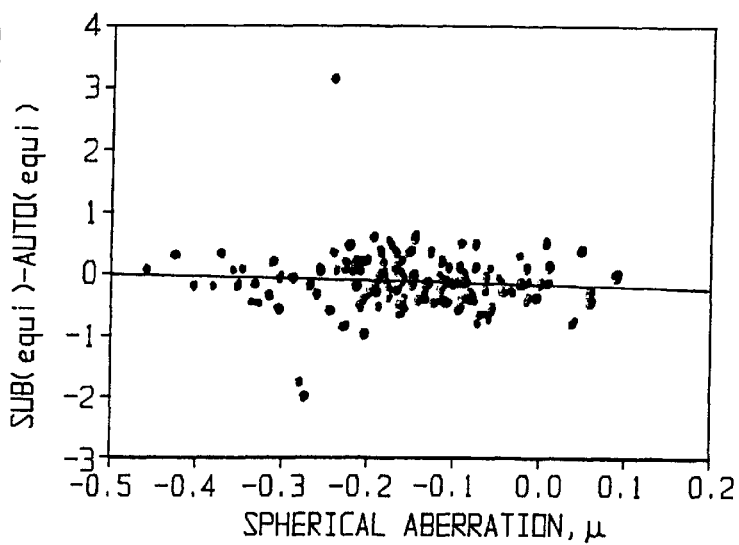
Figure 16C:
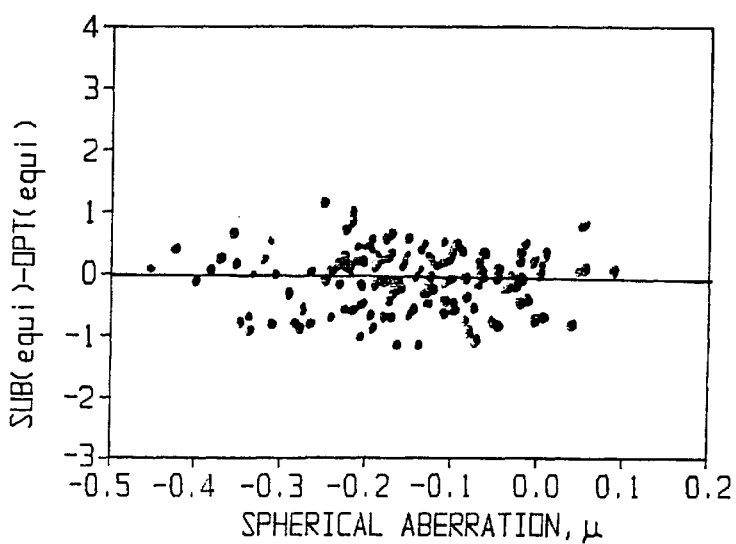

However, the methods differ substantially in the accuracy with which the subjective spherical equivalent can be predicted. FIGS. 16A–16C show the error between the subjective and objective spherical equivalent as a function of the spherical aberration in microns for WF, AUTO and OPT, respectively. The average error (RMSE), in spherical equivalent, across the 146 eyes was as follows:

WF: 0.6±0.7 D
AUTO: 0.5±10.9 D
OPT: 0.4±0.5 D

The percentage of subjects with error in spherical equivalent in excess of 1 D was as follows:

WF: 10%
AUTO: 2%
OPT: 2%

The following can be concluded about the spherical equivalent prediction. First, WF is clearly worse than AUTO and OPT, and their failure increases with the aberrations. Second, AUTO and OPT are similar, although OPT is better (see RMSE and the standard deviation).

Figure 17A:
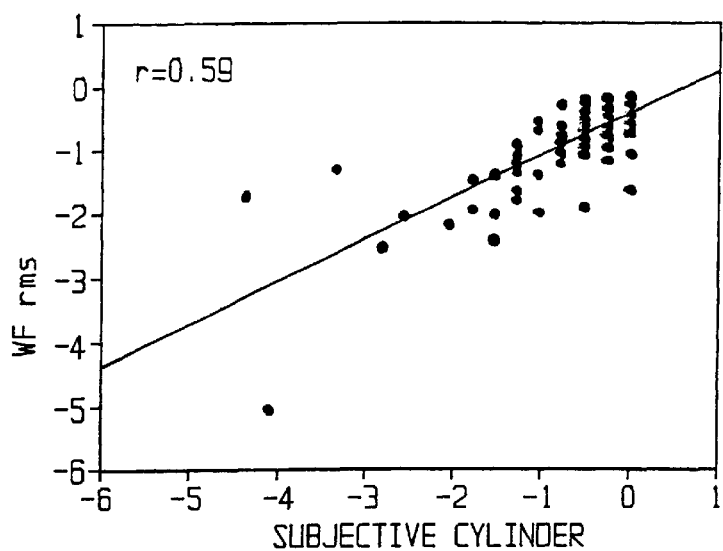
FIGS. 17A–17C show the correlation between the subjective and objective cylinder for the same experimental results.
Figure 17B:
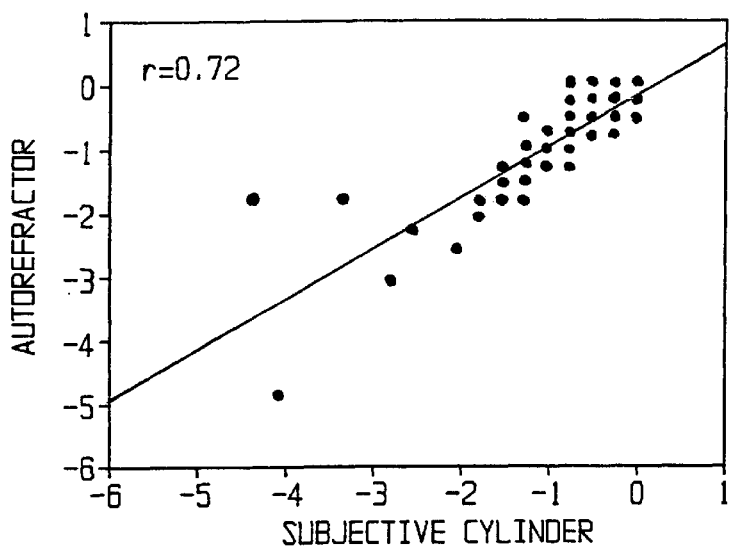
Figure 17C:
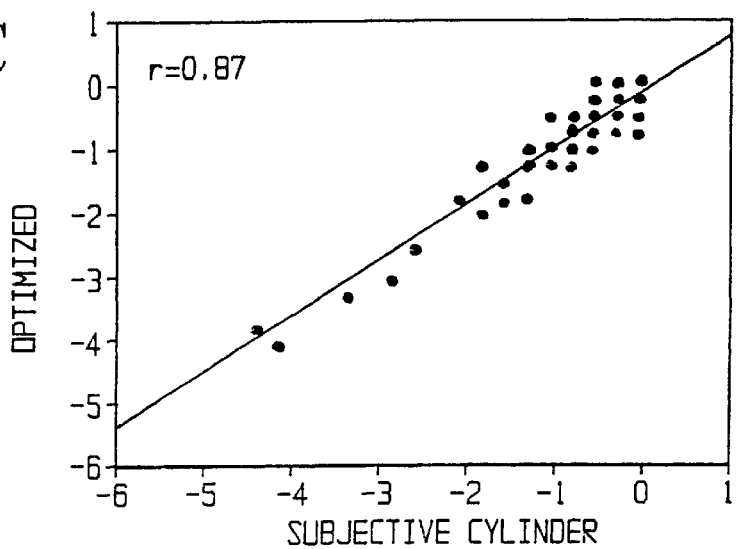

FIGS. 17A–17C show the correlation between subjective and objective cylinder in diopters for WF, AUTO, and OPT, respectively. As can be seen, OPT offers the best correlation and the slope closest to one.

Figure 18A:
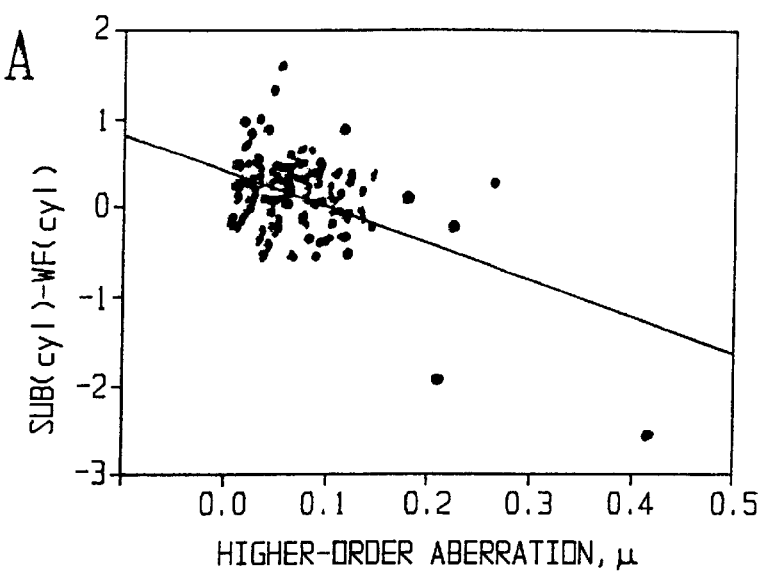
FIGS. 18A–18C show the error between subjective and objective cylinder as a function of the amount of higher order aberrations for the same experimental results.
Figure 18B:
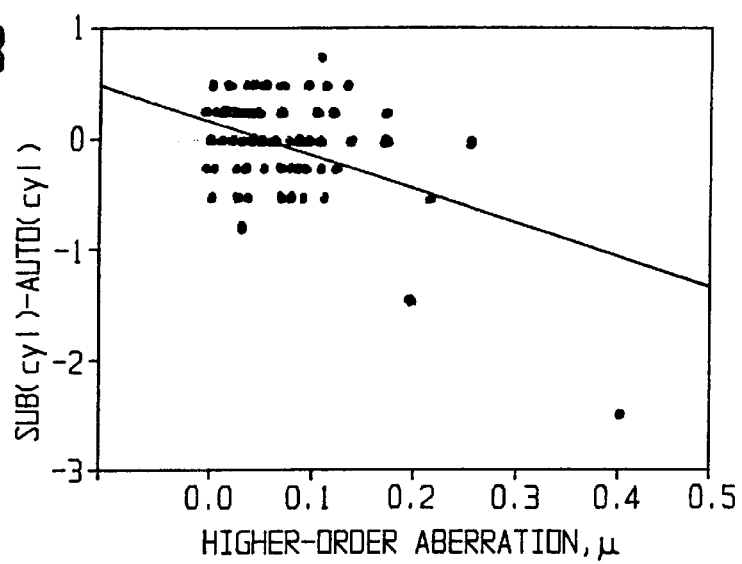
Figure 18C:
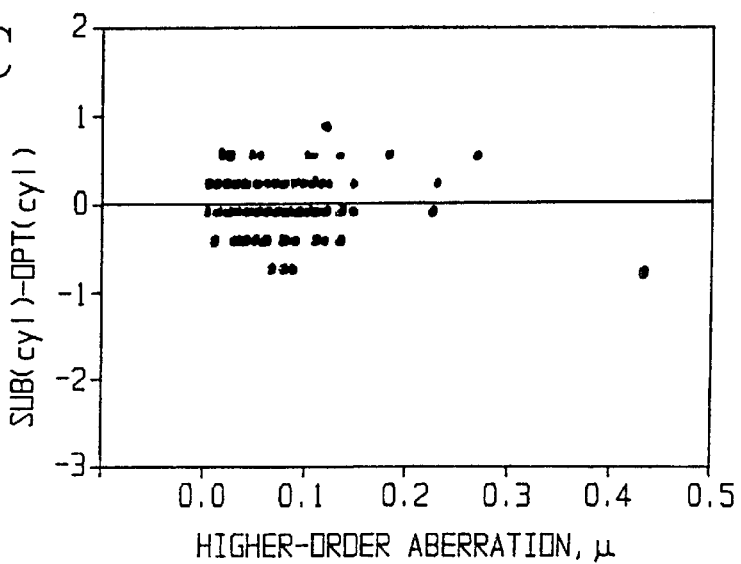

FIGS. 18A–18C show the error between subjective and objective cylinder as a function of the amount of higher order aberrations in microns for WF, AUTO and OPT, respectively. WF and AUTO are aberration-dependent, but OPT is not.

Figure 19A:
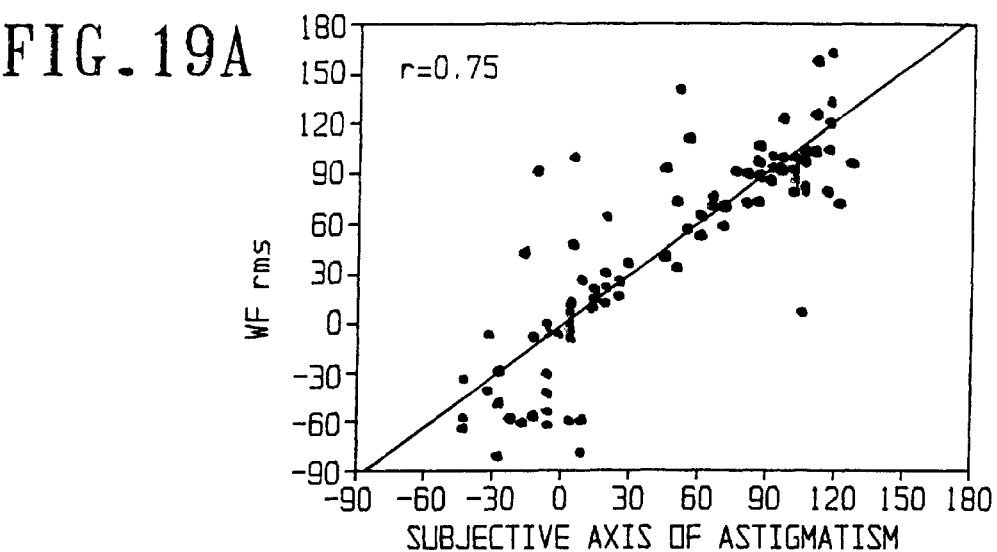
FIGS. 19A–19C show the correlation between the subjective and objective axes of astigmatism for the same experimental results.
Figure 19B:
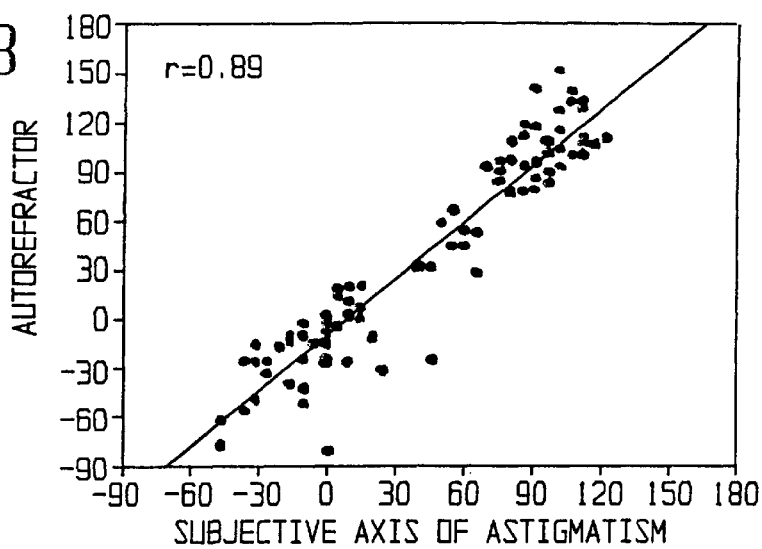
Figure 19C:
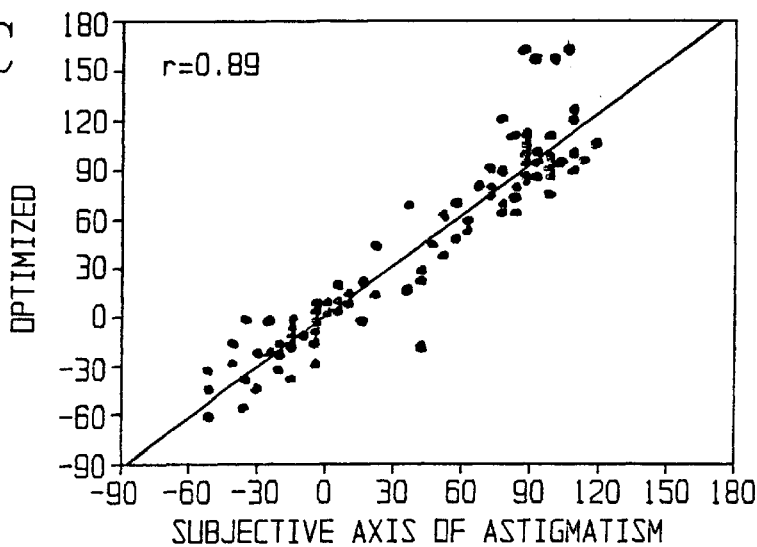

FIGS. 19A–19C show the correlation between subjective and objective axis of astigmatism in degrees for WF, AUTO, and optimization (OPT), respectively. The average error (RMSE) in cylinder is as follows:

WF: 0.6±0.8 D
AUTO: 0.4±0.7 D
OPT: 0.2±0.3 D

The average error (RMSE) in axis is as follows:

WF: 29±43
AUTO: 21±31
OPT: 17±27

The percentage of subjects for whom the error in cylinder exceeds 0.5 D is as follows:

WF: 14%
AUTO: 3%
OPT: <1%

The above figures show that OPT is better than WF or AUTO. They also show that WF and AUTO fail depending on aberrations, while OPT captures the influence of aberrations.

The experimental results presented above allow the following observations. Aberrations influence the ocular refraction. The average error with the metric optimization method (OPT) is lower than 0.4 D for sphere and lower than 0.25 D for cylinder. The errors for the whole population are less than 1 D for sphere and less than 0.5 D for cylinder.

The WF method leaves a significant fraction of the population with errors larger than 1 D for sphere and 0.5 D for astigmatism. The errors in sphere and cylinder with that method depend on the amount of other aberrations.

AUTOrefractometer predicts the sphere reasonably well, but the error in cylinder depends on the aberrations. OPT is better that AUTO.

When OPTimization is used, the error in sphere and the error in astigmatism do not depend on aberrations. The fact that the error of the prediction with metric optimization (OPT) does not depend on the aberrations such as spherical aberration indicates that the method correctly takes into account the effect of those aberrations.

Even for eyes with small amounts of aberrations, the pupil plane method shows errors. That means that there is a variability due to factors others than aberrations. The OPT method reduces the error due to aberrations, but not below the limit of experimental variability. It is anticipated that OPT would have performed even better had pupil size been accurately measured and taken into account in computing OPT. Indeed, one of the advantages of refracting the eye from wave front sensing instead of an autorefractor is that the refraction can be computed for any desired pupil size.

Perhaps the variability is caused partly by the precision of subjective refraction, and partly by the fact that the measurements in the subject population were done without paralyzing the accommodation, which can easily introduce errors of 0.25–0.5 D. The WA is relatively robust to small changes in accommodation except coefficient $c_4$. That could explain why the cylinder can be predicted by metric optimization with precision higher that 0.25 D), but the sphere can be predicted with less precision. Actually the WA of one person's eye measured in one city was similar to that of the same eye taken in another city, but with changes in defocus. If experimental errors in $c_4$ of the WA are present, that variability cannot be reduced with any method. The better the accuracy in the WA data, the better the coefficients can be used to predict the refraction. Another possible source of error is a bias in subjective refraction from the autorefraction results, just because the subjective refraction trials sometimes start with the values obtained from autorefraction.

While a preferred embodiment of the present invention has been set forth above, those skilled in the art who have reviewed the present disclosure will readily appreciate that other embodiments can be realized within the scope of the invention. For example, numerical values given throughout the specification are illustrative rather than limiting. Also, any reliable wavefront detector can be used, such as a Shack-Hartmann detector, a scanning detector or an aberroscope. Also, any method of correcting vision can be used with the present invention. Therefore, the present invention should be construed as limited only by the appended claims.

We claim:

1. A method for determining a correction to correct for aberrations in an eye of a patient, the method comprising:
   (a) receiving data signals representing the aberrations; and
   (b) from the data signals, determining the correction such that when the correction is applied to the eye, an image-quality metric on an image plane of the eye is objectively optimized.

2. The method of claim 1, wherein the image-quality metric comprises a Strehl ratio.

3. The method of claim 1, wherein the image-quality metric comprises a function of at least one metric on a pupil plane of the eye.

4. The method of claim 1, wherein the image-quality metric comprises an entropy of a point spread function determined from the data signals.

5. The method of claim 1, wherein the image-quality metric comprises an encircled energy.

6. The method of claim 1, wherein the image-quality metric comprises a variance of a Appoint spread function determined from the data signals.

7. The method of claim 1, wherein the image-quality metric comprises an integral of a modulation transfer function of the eye determined from the data signals.

8. The method of claim 1, wherein the image-quality metric comprises an integral of a contrast sensitivity function of the eye determined from the data signals.

9. The method of claim 1, wherein step (a) is performed with a Shack-Hartmann detector.

10. The method of claim 1, wherein step (b) comprises:
    (i) defining a search space comprising a plurality of sets of coefficients;
    (ii) calculating the image-quality metric for each of the sets of coefficients in the search space;
    (iii) selecting the optimum value of the image-quality metric from all values of the image-quality metric calculated in step (b)(ii), and
    (iv) determining the correction in accordance with one of the plurality of sets of coefficients for which the optimum value of the image-quality metric is calculated in step (b)(iii).

11. The method of claim 10, wherein the plurality of sets of coefficients are sets of Zernike coefficients for second-order aberrations.

12. The method of claim 10, wherein the image quality metric is calculated in step (b)(ii) from a product of an eye pupil function which includes n aberrations and is determined from the data signals received in step (a) and a correcting pupil function which includes m aberrations, m<n, and is calculated from each of the sets of coefficients independently of the data signals.

13. The method of claim 10, wherein the image-quality metric comprises a Strehl ratio.

14. The method of claim 10, wherein the image-quality metric comprises a function of at least one metric on a pupil plane of the eye.

15. The method of claim 10, wherein the image-quality metric comprises an entropy of a point spread function determined from the data signals.

16. The method of claim 10, wherein the image-quality metric comprises an encircled energy.

17. The method of claim 10, wherein the image-quality metric comprises a variance of a point spread function determined from the data signals.

18. The method of claim 10, wherein the image-quality metric comprises an integral of a modulation transfer function of the eye determined from the data signals.

19. The method of claim 10, wherein the image-quality metric comprises an integral of a contrast sensitivity function of the eye determined from the data signals.

20. The method of claim 10, wherein step (a) is performed with a Shack-Hartmann detector.

21. The method of claim 10, wherein the correction comprises a correction for second-order aberrations.

22. The method of claim 21, wherein the second-order aberrations consist only of defocus.

23. The method of claim 10, wherein the correction comprises a correction for third-order aberrations.

24. The method of claim 10, wherein the correction comprises a correction for fourth-order aberrations.

25. The method of claim 10, further comprising forming a lens to provide the correction.

26. The method of claim 10, further comprising performing surgery on the eye to provide the correction.

27. The method of claim 10, further comprising providing adaptive optics to provide the correction.

28. The method of claim 10, further comprising synthesizing an image that the patient would see with the correction applied to the eye.

29. The method of claim 10, wherein the correction corrects fewer than all of the aberrations that are detected.

30. The method of claim 1, wherein the correction comprises a correction for second-order aberrations.

31. The method of claim 30, wherein the second-order aberrations consist only of defocus.

32. The method of claim 1, wherein the correction comprises a correction for third-order aberrations.

33. The method of claim 1, wherein the correction comprises a correction for fourth-order aberrations.

34. The method of claim 1, further comprising forming a lens to provide the correction.

35. The method of claim 1, further comprising performing surgery on the eye to provide the correction.

36. The method of claim 1, further comprising providing adaptive optics to provide the correction.

37. The method of claim 1, further comprising synthesizing an image that the patient would see with the correction applied to the eye.

38. The method of claim 1, wherein the correction corrects fewer than all of the aberrations that are detected.

39. A system for determining a correction to correct for aberrations in an eye of a patient, the system comprising:
    a sensing device for illuminating a retina of the eye, receiving light reflected from the retina, producing data signals representing the aberrations from the light reflected from the retina, and outputting the data signals; and a computing device for:
(a) receiving the data signals; and
(b) from the data signals, determining the correction such that when the correction is applied to the eye, an image-quality metric on an image plane of the eye is objectively optimized.

40. The system of claim 39, wherein the image-quality metric comprises a Strehl ratio.

41. The system of claim 39, wherein the image-quality metric comprises a function of at least one metric on a pupil plane of the eye.

42. The system of claim 39, wherein the image-quality metric comprises an entropy of a point spread function determined from the data signals.

43. The system of claim 39, wherein the image-quality metric comprises an encircled energy.

44. The system of claim 39, wherein the image-quality metric comprises a variance of a point spread function determined from the data signals.

45. The system of claim 39, wherein the image-quality metric comprises an integral of a modulation transfer function of the eye determined from the data signals.

46. The system of claim 39, wherein the image-quality metric comprises an integral of a contrast sensitivity function of the eye determined from the data signals.

47. The system of claim 39, wherein the sensing device comprises a Shack-Hartmann detector.

48. The system of claim 39, wherein the computing device determines the correction by:
(i) defining a search space comprising a plurality of sets of coefficients;
(ii) calculating the image-quality metric for each of the sets of coefficients in the search space;
(iii) selecting the optimum value of the image-quality metric from all values of the image-quality metric calculated in step (ii); and
(iv) determining the correction in accordance with one of the plurality of sets of coefficients for which the optimum value of the image-quality metric is calculated in step (iii).

49. The system of claim 48, wherein the plurality of sets of coefficients are sets of Zernike coefficients for second-order aberrations.

50. The system of claim 48, wherein the image quality metric is calculated in step (ii) from a product of an eye pupil function which includes n aberrations and is determined from the data signals received in step (a) and a correcting pupil function which includes m aberrations, m<n, and is calculated from each of the sets of coefficients independently of the data signals.

51. The system of claim 48, wherein the image-quality metric comprises a Strehl ratio.

52. The system of claim 48, wherein the image-quality metric comprises a function of at least one metric on a pupil plane of the eye.

53. The system of claim 48, wherein the image-quality metric comprises an entropy of a point spread function determined from the data signals.

54. The system of claim 48, wherein the image-quality metric comprises an encircled energy.

55. The system of claim 48, wherein the image-quality metric comprises a variance of a point spread function determined from the data signals.

56. The system of claim 48, wherein the image-quality metric comprises an integral of a modulation transfer function of the eye determined from the data signals.

57. The system of claim 48, wherein the image-quality metric comprises an integral of a contrast sensitivity function of the eye determined from the data signals.

58. The system of claim 48, wherein the sensing device comprises a Shack-Hartmann detector.

59. The system of claim 48, wherein the correction comprises a correction for second-order aberrations.

60. The system of claim 59, wherein the second-order aberrations consist only of defocus.

61. The system of claim 48, wherein the correction comprises a correction for third-order aberrations.

62. The system of claim 48, wherein the correction comprises a correction for fourth-order aberrations.

63. The system of claim 48, further comprising a device that receives information representing the correction from the computing device and forms a lens to provide the correction.

64. The system of claim 48, further comprising a device that receives information representing the correction from the computing device and performs surgery on the eye to provide the correction.

65. The system of claim 48, further comprising a device that receives information representing the correction from the computing device and provides adaptive optics to provide the correction.

66. The system of claim 48, further comprising a device that receives information representing the correction from the computing device and synthesizes an image that the patient would see with the correction applied to the eye.

67. The system of claim 48, wherein the correction corrects fewer than all of the aberrations that are detected.

68. The system of claim 39, wherein the correction comprises a correction for second-order aberrations.

69. The system of claim 68, wherein the second-order aberrations consist only of defocus.

70. The system of claim 39, wherein the correction comprises a correction for third-order aberrations.

71. The system of claim 39, wherein the correction comprises a correction for fourth-order aberrations.

72. The system of claim 39, further comprising a device that receives information representing the correction from the computing device and forms a lens to provide the correction.

73. The system of claim 39, further comprising a device that receives information representing the correction from the computing device and performs surgery on the eye to provide the correction.

74. The system of claim 39, further comprising a device that receives information representing the correction from the computing device and provides adaptive optics to provide the correction.

75. The system of claim 39, further comprising a device that receives information representing the correction from the computing device and synthesizes an image that the patient would see with the correction applied to the eye.

76. The system of claim 39, wherein the correction corrects fewer than all of the aberrations that are detected.

* * * * *